(12) United States Patent
Tamai et al.

(10) Patent No.: US 8,353,849 B2
(45) Date of Patent: Jan. 15, 2013

(54) GUIDE WIRE

(75) Inventors: Noriyuki Tamai, Fujinomiya (JP);
Katsuhiro Shirakawa, Fujinomiya (JP);
Hiroshi Yagi, Fujinomiya (JP)

(73) Assignee: Terumo Kabushiki Kaisha, Shibuya-ku, Tokyo (JP)

( * ) Notice: Subject to any disclaimer, the term of this patent is extended or adjusted under 35 U.S.C. 154(b) by 224 days.

(21) Appl. No.: 12/188,910

(22) Filed: Aug. 8, 2008

(65) Prior Publication Data

US 2008/0306468 A1 Dec. 11, 2008

Related U.S. Application Data

(63) Continuation of application No. PCT/JP2007/054266, filed on Mar. 6, 2007.

(30) Foreign Application Priority Data

Mar. 6, 2006 (JP) .................................. 2006-059902
Apr. 28, 2006 (JP) .................................. 2006-125809

(51) Int. Cl.
*A61B 5/00* (2006.01)
(52) U.S. Cl. ...................................................... 600/585
(58) Field of Classification Search .................. 600/585, 600/434, 435; 604/164.13, 523–284
See application file for complete search history.

(56) References Cited

U.S. PATENT DOCUMENTS

| 3,757,768 | A | | 9/1973 | Kline |
| 4,827,941 | A | | 5/1989 | Taylor et al. |
| 4,925,445 | A | * | 5/1990 | Sakamoto et al. ............. 604/528 |
| 5,365,942 | A | * | 11/1994 | Shank ............................ 600/585 |
| 6,524,301 | B1 | | 2/2003 | Wilson et al. |
| 7,048,695 | B1 | | 5/2006 | Schwager |
| 2005/0113862 | A1 | * | 5/2005 | Besselink et al. ............. 606/200 |
| 2005/0228418 | A1 | | 10/2005 | Noriega et al. |

FOREIGN PATENT DOCUMENTS

| EP | 0 778 044 A2 | 6/1997 |
| EP | 0 778 044 A3 | 6/1997 |
| EP | 778044 A2 * | 6/1997 |
| JP | 61-7736 U | 1/1986 |
| JP | 2-4390 A | 1/1990 |
| JP | 11-076415 A | 3/1999 |
| JP | 11-76415 A | 3/1999 |

(Continued)

OTHER PUBLICATIONS

Extended European Search Report issued Mar. 9, 2009 in EP 07 71 5234.6, Munich, DE.

*Primary Examiner* — Max Hindenburg
*Assistant Examiner* — John Pani
(74) *Attorney, Agent, or Firm* — Buchanan Ingersoll & Rooney PC

(57) ABSTRACT

The guide wire is a guide wire includes a distal portion and a main body portion. This guide wire is provided with a first curve portion; a second curve portion included on the distal side of aforesaid first curve portion and curved to the opposite direction with respect to aforesaid first curve portion; a third curve portion included on the distal side of aforesaid second curve portion and curved to the opposite direction with respect to aforesaid second curve portion, wherein a line contacting with both aforesaid first curve portion and aforesaid third curve portion has an obtuse angle with respect to an axis line of aforesaid main body portion.

20 Claims, 17 Drawing Sheets

FOREIGN PATENT DOCUMENTS

| | | |
|---|---|---|
| JP | 2003-508168 | 3/2003 |
| JP | 2003-530132 A | 10/2003 |
| JP | 2004-181184 A | 7/2004 |
| WO | WO 96/19148 A1 | 6/1996 |
| WO | WO 98/37923 A2 | 9/1998 |
| WO | WO 98/37923 A3 | 9/1998 |
| WO | WO 99/23958 A1 | 5/1999 |
| WO | WO 99/52421 A1 | 10/1999 |
| WO | WO 00/53250 A1 | 9/2000 |
| WO | WO02/078779 A1 | 10/2002 |
| WO | WO 2004/110519 A2 | 12/2004 |
| WO | WO 2004/110519 A3 | 12/2004 |

* cited by examiner

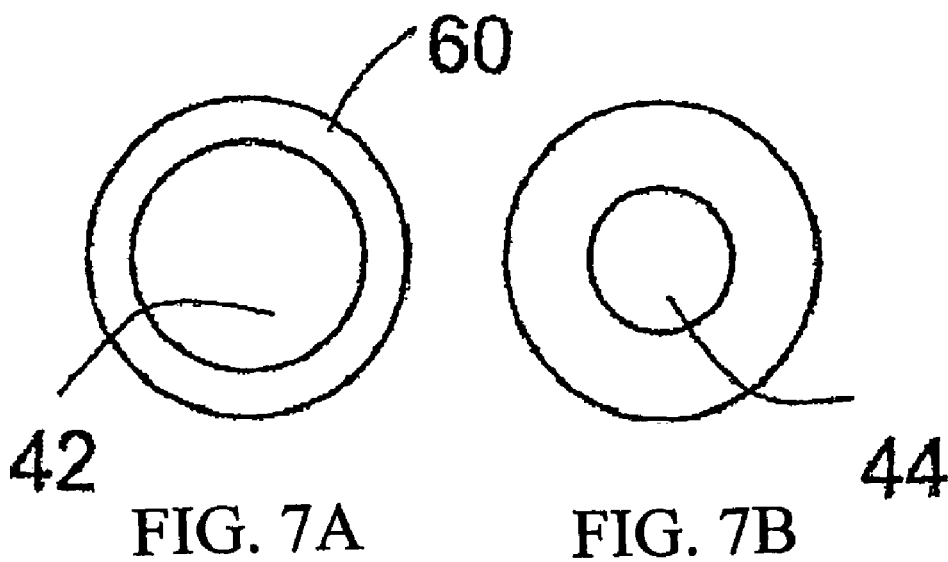
FIG. 7A  42    FIG. 7B  44
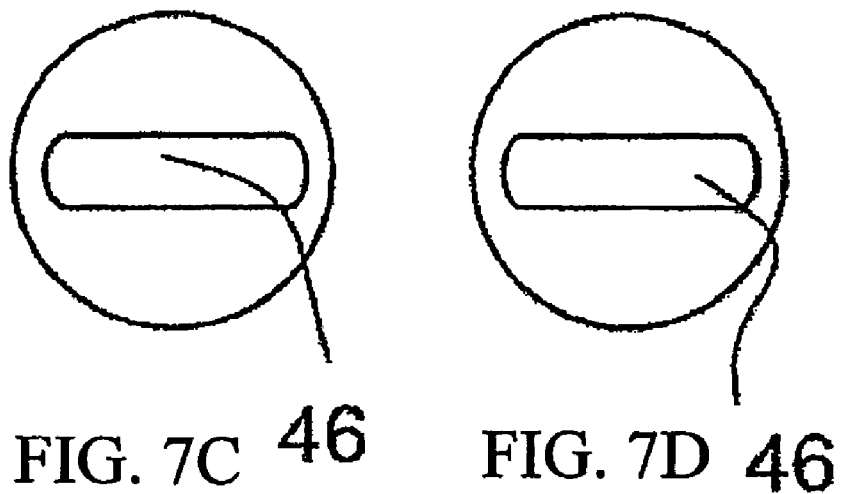
FIG. 7C  46    FIG. 7D  46
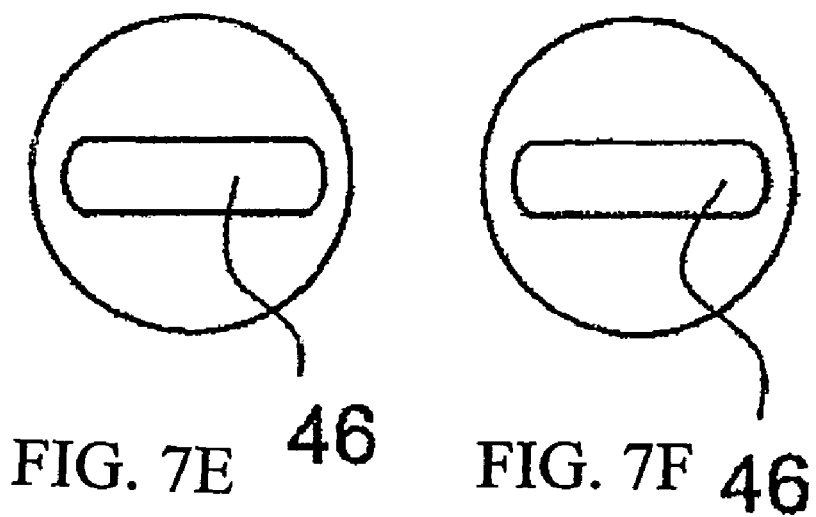
FIG. 7E  46    FIG. 7F  46

GUIDE WIRE

TECHNICAL FIELD

This application is a continuation of International Application No. PCT/JP2007/054266 filed on Mar. 6, 2007, the entire content of which is incorporated herein by reference. This application also claims priority under 35 U.S.C. §119 based on Japanese Application No. 2006-059902 filed on Mar. 6, 2006 and Japanese Application No. 2006-125809 filed on Apr. 28, 2006.

TECHNOLOGICAL FIELD

The present invention generally relates to a medical implement. More specifically, the invention pertains to a guide wire for introducing and aiming a medical device such as a catheter, an introducer kit or the like used during medical treatment or diagnosis to a desired region in a blood vessel.

BACKGROUND DISCUSSION

A guide wire is used to introduce and indwell a medical device such as a catheter, an introducer kit or the like in a blood vessel when executing diagnosis and medical treatment of the blood vessel percutaneously. It was common in the past that the region at which a medical device such as a catheter or the like was introduced into a blood vessel was the femoral (FEMORAL). In recent years though, the introduction region is shifting to a brachial (BRACHIAL) and, in particular, to a radial (RADIAL) in order to lighten the burden on the patient. There has thus been a desire for a guide wire, including for example a guide wire with a J-shape distal tip, which possesses quite good steerability characteristics while also being capable of being used safely in a blood vessel of an arm portion that often includes branches and meanders.

In the past, when a guide wire with a J-shape distal tip was inserted into an introducing needle, a catheter or the like, a supplemental tool (inserter) has been used for making the insertion easier. However, in a case, in particular, in which the curvature radius of the curved portion of the J-shape is relatively small, the operation for inserting a guide wire once again into the inserter when exchanging the catheter or the like was complicated.

To address this, there is disclosed a tool in which the need for a supplemental tool when inserting a wire into an introducing needle, a catheter, a sheath or the like is unnecessary. This is accomplished by designing the angle formed by the extended line in the direction of the distal tip linear portion and the wire base line to be 40 to 700 with respect to the distal shape of the guide wire. An example of this is described in Patent Document 1 identified below.

Patent Document 2 identified below discloses a guide wire having a distal shape preformed as a multi-bending shape for use in entering a side opening of a tube for medical treatment. Also, Patent document 3 identified below discloses a guide wire which includes two curve portions facing different directions in order to control the direction of the distal tip of the guide wire.

In case of a guide wire whose distal tip is formed to possess a J-shape as seen in Patent Document 1, it is necessary to stretch the J-shaped distal portion once and thereafter insert it into an introducing needle, catheter or a sheath. It thus often happens that the steerability of the guide wire is not very good.

Also, with respect to the guide wire disclosed in Patent Document 2, the inner diameter of the tube for medical treatment to be used is known beforehand, so that in when using a guide wire having a shape corresponding to the inner diameter thereof, it is difficult for the guide wire to come out from the side opening of the tube for medical treatment. However, the blood vessel possesses a different diameter depending on the individual organism, region or the like, so that in case of using the guide wire of Patent Document 2 for a blood vessel, it is necessary to separately use a guide wire which has a different shape for every patient or for every region so as not to erroneously-enter into a side-branch of a blood vessel. The guide wire disclosed in Patent Document 3 is not as likely to erroneously-enter into a side-branch in the case of a blood vessel having a thin side-branch. But in the case of a blood vessel having a thick side-branch, it happens that the guide wire may erroneously-enter into the side-branch and it becomes difficult to reach the aimed region and therefore, the steerability is bad.

With respect to the guide wire described in Patent Document 4, the shape of the guide wire is formed to be such a shape that it is possible to select branches of both the vascular channels having large and small diameters. However, it is relatively easy to erroneously-enter into a branch for that reason and it happens that it will spend time for the operation after all in case of introducing it from the radial as mentioned above.

Further, Patent Document 5 identified below discloses a guide wire having an S-shape distal shape to introduce it into a blood vessel branch. But a guide wire such as that having an S-shape distal tip faces the hand direction at the most distal tip thereof, so that it is difficult to insert it into an introducing needle or a catheter, and so it is necessary to also use an inserter.

[Patent Document 1] Japanese Unexamined Patent Publication No. 2004-181184.

[Patent Document 2] Japanese Unexamined Patent Publication No. H11-76415.

[Patent Document 3] Japanese Unexamined Patent Publication No. 2003-530132.

[Patent Document 4] Japanese Unexamined Patent Publication No. 2003-508168.

[Patent Document 5] Japanese Utility Model Patent Publication No. S61-7736.

SUMMARY

According to one aspect, a guide wire comprises an elongated member comprised of a straight main body portion and a curved distal portion positioned on a distal side of the straight main body portion, wherein the curved distal portion of the elongated member comprises a first curve portion, a second curve portion and a third curve portion. The first curve portion is more flexible than the main body portion, and the first curve portion immediately follows the distal end of the straight main body portion. The second curve portion is positioned distally of the first curve portion, and the second curve portion curves in a direction of curvature that is opposite the direction of curvature of the first curve portion. The second curve portion is more flexible than the first curve portion, and the third curve portion is positioned distally of the second curve portion. The third curve portion curves in a direction opposite the direction of curvature of the second curve portion. A line contacting both the first curve portion and the third curve portion forms an obtuse angle with respect to the axis of the main body portion.

In accordance with another aspect, a guide wire comprises an elongated member comprised of a main body portion and a distal portion positioned on a distal side of the main body portion, wherein the elongated member comprises a first curve portion curving in a direction of curvature, a second curve portion and a third curve portion. The second curve portion is positioned on the distal side of the first curve portion and curves in a direction of curvature that is opposite the direction of curvature of the first curve portion. The third curve portion is positioned on the distal side of the second curve portion and curves in a direction opposite the direction of curvature of the second curve portion. A line contacting both the first curve portion and the third curve portion forms an obtuse angle with respect to the axis of the main body portion.

This construction of the guide wire results in a guide wire whose steerability is quite good when operating the guide wire. In particular, as a guide wire which is to be introduced from a radial artery of a wrist, it is difficult to erroneously-enter into side-branches with respect to inter-individual differences and various blood vessel diameters reaching until the left ventricle and it is possible to insert it relatively smoothly to the aimed region.

It is preferable for the most distal tip of the guide wire to be positioned between the line contacting the first and second curve portions and a line which is parallel with such line and contacts the second curve portion.

Thus, when inserting a guide wire into a tubular medical device such as, for example, an introducing needle, a catheter, a sheath or the like, it is possible to execute the insertion operation relatively easily and reliably.

The direction of the portion of the guide wire shifting from the first curve portion to the second curve portion preferably forms a larger angle with respect to the axis line of the main body portion compared with the angle formed by the direction in which the most distal tip is directed with respect to the axis line of the main body portion.

With this construction, when inserting a guide wire into a tubular medical device such as, for example, an introducing needle, a catheter, a sheath or the like, it is possible to execute the insertion operation quite easily and also with relative certainly.

The portion of the guide wire shifting from the second curve portion to the third curve portion can be parallel to the axis line of the main body portion.

Thus, when inserting a guide wire into a tubular medical device such as, for example, an introducing needle, a catheter, a sheath or the like, it is possible to relatively easily and reliably execute the insertion operation.

It is also possible to configure the guide wire so that the portion of the guide wire shifting from the second curve portion to the third curve portion to be oriented in a direction diverging from or converging towards the axis line of the main body portion in the distal direction.

This configuration can also help facilitate the insertion operation of inserting the guide wire into a tubular medical device such as, for example, an introducing needle, a catheter, a sheath or the like.

The guide wire disclosed here includes a distal portion and a main body portion, with the distal portion being provided with a curve portion. The steerability of the guide wire is thus quite good when operating the guide wire.

The first curve portion is preferably more flexible (has a higher flexibility) than the main body portion, and the second curve portion is preferably more flexible (has a higher flexibility) than the first curve portion.

When inserting a guide wire into a curved blood vessel, it is thus possible for the distal portion of the guide wire to follow the shape of the blood vessel. Consequently, the steerability when operating the guide wire is improved. Even if the most distal tip of the guide wire gets into a branch, it turns around, advances in the main blood vessel and does not erroneously-enter into a branch.

According to another aspect, a guide wire comprises an elongated member comprised of a main body portion and a distal portion positioned on a distal side of the main body portion, a first curve portion provided at the distal portion of the elongated member, with the first curve portion curving in a direction of curvature, a second curve portion positioned distally of the first curve portion and curving in a direction of curvature that is opposite the direction of curvature of the first curve portion, and a third curve portion positioned distally of the second curve portion and curved in a direction opposite the direction of curvature of the second curve portion. The first curve portion possesses a higher flexibility than the main body portion, and the second curve portion possesses a higher flexibility than the first curve portion.

The guide wire is thus constructed in a way such that the steerability of the guide wire is relatively excellent when operating the guide wire. Even if the most distal tip of the guide wire gets into a branch, it turns around, advances in the main blood vessel and does not erroneously-enter into a branch.

It is preferable for the third curve portion to have a higher flexibility, or the same flexibility, compared with the second curve portion.

With this construction, when inserting the guide wire into a curved blood vessel, it is possible for the distal portion of the guide wire to follow the shape of the blood vessel. Consequently, the steerability when operating a guide wire is improved.

The guide wire is preferably composed of a core wire including a distal portion and a coating portion which covers at least the distal portion of the core wire and which is constituted by a resin. This helps improve the steerability of the guide wire when operating the guide wire.

The distal portion of the core wire of the guide wire preferably includes a flat portion. Thus, higher flexibility is exhibited at the flat portion.

It is preferable for the core wire at which the third curve portion is positioned to be a flat portion and for the third curve portion to have a higher flexibility compared with the second curve portion. Thus, much higher flexibility is exhibited at the flat portion and consequently, the steerability of the guide wire is improved when operating the guide wire.

BRIEF DESCRIPTION OF THE DRAWING FIGURES

FIGS. 7A-7F are cross-sectional views of portions of another embodiment of a guide wire taken along section lines corresponding in position to the correspondingly lettered section lines in FIG. 5.

DETAILED DESCRIPTION

Figure 1:
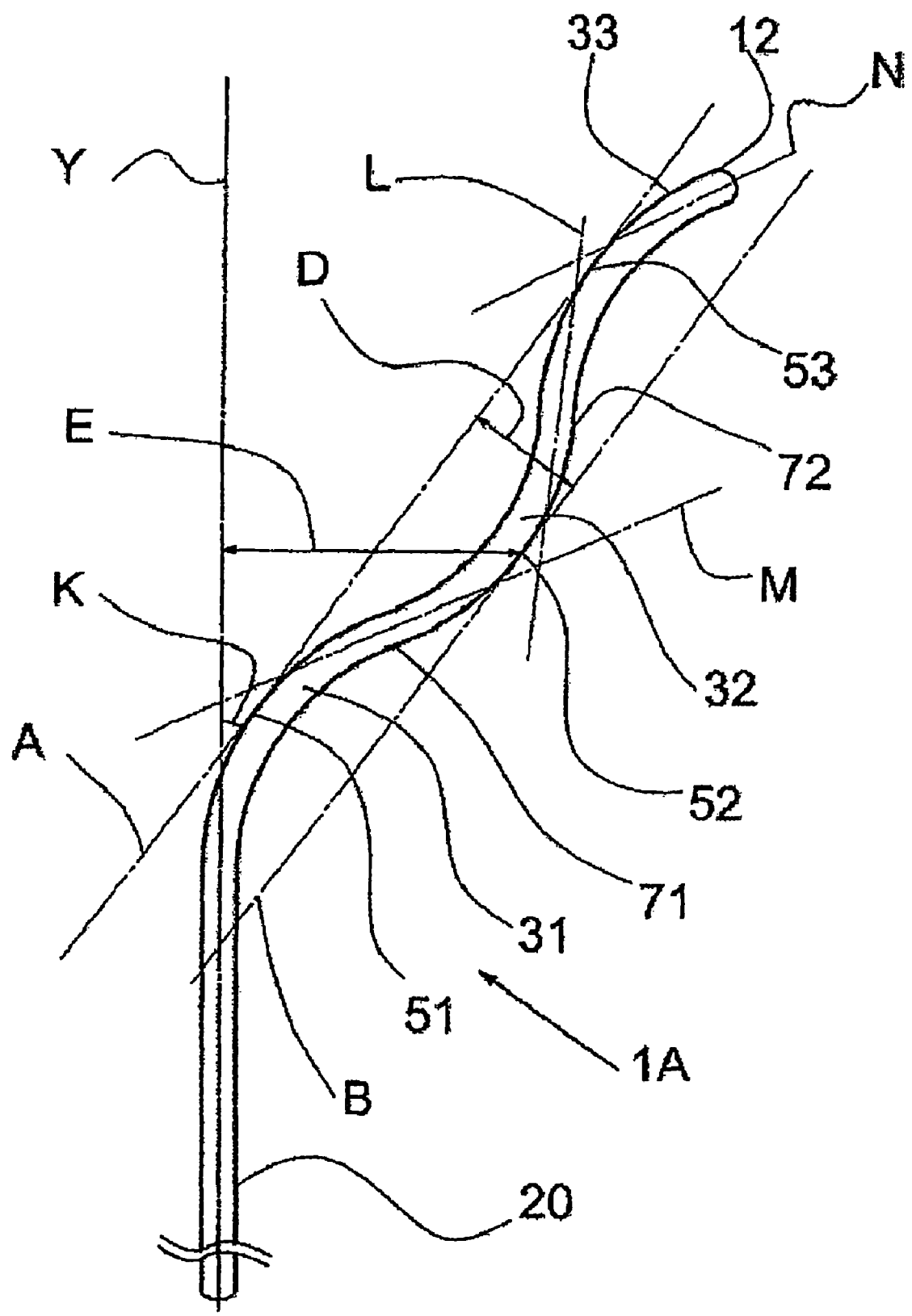
FIG. 1 is a partially enlarged side view showing one embodiment of a guide wire disclosed here.

A guide wire according to one embodiment disclosed here is illustrated in FIG. 1. The guide wire 1A according to this embodiment is a guide wire comprised of an elongated member composed of a distal portion 10 and a main body portion 20. The elongated member, specifically the distal portion 10 of the guide wire, includes multiple curve portions. More specifically, the distal portion 10 includes a first curve portion 31 subsequent to or immediately following the distal side of the main body portion 20 and a second curve portion 32 positioned on the distal side of the first curve portion 31 and curved in a direction opposite the direction of curvature of the first curve portion 31. It is also possible to include a linear (i.e., non-curved) portion between the first curve portion 31 and the second curve portion 32 so that the two curved portions 31, 32 are separated by a portion which is not curved. In the illustrated embodiment, the main body portion 20 is straight or linear, with the distal end of the straight main body portion directly merging into the first curve portion.

The distal portion 10 of the guide wire further comprises a third curve portion 33 positioned on the distal side of the second curve portion 32 and curved in a direction opposite the direction of curvature of the second curve portion 32. Once again, it is also possible to include a linear (i.e., non-curved) portion between the second curve portion 31 and the third curve portion 32 so that the two curved portions 32, 33 are separated by a portion which is not curved. The distal side of the third curve portion 33 is terminated by the most distal tip 12. The first curve portion 31, the second curve portion 32 and the third curve portion 33 are constituted in the same plane.

The guide wire 1A is configured so that a line A contacting both the first curve portion 31 and the third curve portion 32 forms an obtuse angle with respect to the central axis (line Y) of the main body portion 20 in the guide wire's natural state (an obtuse angle extending from the line A to the axis (line) Y of the main body portion 20 in the clockwise direction). Here, "natural state" means a state in which an external force is not applied to the guide wire 1A. The axis (axis line) Y refers to the central axis of the portion (linear or straight portion) of the guide wire proximally adjoining the first curve portion 31. It is preferable for the angle K between the line A and the axis line Y to be 20 to 45 degrees, more preferably 25 to 42 degrees. The line A referenced above is a line A passing through a contact point 51 of the first curve portion 31 and a contact point 53 of the third curve portion 33. The contact point 51 represents the vertex of the first curve portion 31 while the contact point 53 represents the vertex of the second curve portion 33. The contact points 51, 53 are also the outwardmost point in the direction of curvature of the first and third curve portions 31, 33 respectively.

The most distal tip 12 of the guide wire 1A is positioned between the line A, which contacts both the first curve portion 31 and the third curve portion 32, and a line B which is parallel with the line A and contacts the second curve portion 32. The line B passes through a contact point 52 of the second curve portion 32. The contact point 52 is the vertex of the second curve portion 32. Also, the contact point 52 represents the outwardmost point in the direction of curvature of the second curve portion 32.

The direction M of the guide wire portion 71 shifting from the first curve portion 31 to the second curve portion 32 (where the direction M is indicated by the central axis of the guide wire portion 71 shifting from the first curve portion 31 to the second curve portion 32) forms an angle with respect to the axis line Y larger than the angle which the direction N of the distal-most tip 12 forms with the axis line Y (where the direction N refers to the central axis of the distal-most tip 12). Thus, the axial centerline M of a portion of the guide wire between the first and second curved portions 31, 32 forms an angle with the axis line Y that is larger than the corresponding angle between the axial centerline N of the distal most portion of the guide wire and the axis line Y. The direction L of a portion 72 of the guide wire shifting from the second curve portion 32 to the third curve portion 33 (where the direction L is indicated by the central axis of the guide wire portion 72 shifting from the second curve portion 32 to the third curve portion 33) is a direction diverging away from the axis line Y in the distal direction. That is, the portion 72 is oriented so that the line L diverges from the axis line Y towards the distal direction (i.e., toward the top of the page in FIG. 1).

It is preferable for the distance D between the line A and the line B to be 2 to 11 mm, more preferably 4 to 9 mm. If the distance D is too small (e.g., smaller than 2 mm), the most distal tip 12 may contact the blood vessel wall when advancing in the blood vessel and there is a higher likelihood for the erroneous-entering, for example to side branches. If the distance D is excessively large (e.g., larger than 11 mm), the distal most tip 12 may contact the blood vessel wall in case of advancing in a comparatively thin blood vessel. It is preferable for the distance E between a vertex 52 of the second curve portion 32 and the axis line Y of the main body portion 20 to be 9 to 16 mm, more preferably 10 to 15 mm. If the distance E is excessively small (e.g., smaller than 9 mm), the second curve portion 32 does not contact the blood vessel wall when advancing in a rather thick blood vessel and the most distal tip 12 will approach or contact the blood vessel wall, in which more chances occur for the erroneous-entering to side-branches. If the distance E is excessively large (e.g., larger than 16 mm), the second curve portion 32 tends to exhibit a state of spreading when advancing in a rather thin blood vessel and the most distal tip 12 is reflexed, in which more chances occur for contact with the blood vessel wall and the possibility of the erroneous-entering becomes high.

The guide wire 1A includes a core wire and a coating portion which covers at least the distal portion of the core wire and which is constituted by a resin. It is preferable for the core wire to be an NiTi alloy wire. It is preferable for the resin of the coating portion to be polyurethane. It is preferable for the front face of the coating portion to be coated with a hydrophilic polymer. The distal portion 10 of the core wire possesses a tapered shape so that the distal portion 10 is more flexible than the main body portion 20.

It is relatively easy for the guide wire 1A to be inserted into an introducing needle, a catheter or a sheath. Specifically, it is possible to relatively easily insert the guide wire 1A into a catheter including a catheter main body of tubular shape having elasticity and a hub installed at the proximal portion of the catheter main body and into the aforesaid hub from the distal side thereof.

Also, the guide wire 1A is not as susceptible to erroneously entering into a side-branch in a blood vessel and it can reach an aimed region quite speedily. Specifically, when inserting the guide wire 1A into a blood vessel and in a case in which the blood vessel thereof is in a straight line shape, the most distal tip 12 of the guide wire 1A is inhibited or prevented from touching the blood vessel wall. Also, in a case in which there exists, at a position of a blood vessel into which the guide wire 1A is inserted, a side-branch (blood vessel) branching from the blood vessel thereof, the distal portion 10 of the guide wire 1A is prevented from entering into the side-branch unwillingly. Thus, it is possible for the guide wire 1A to reach an aimed region in a blood vessel speedily.

Figure 2A:
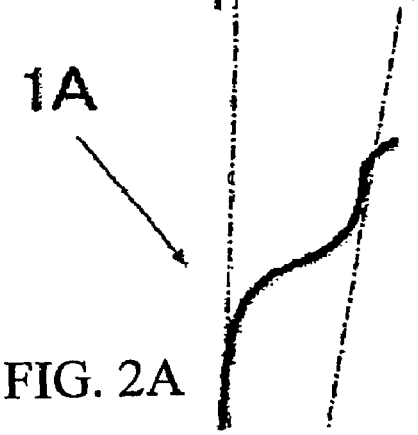
FIGS. 2A-2D are schematic illustrations of other embodiments of a guide wire disclosed here.
Figure 2B:
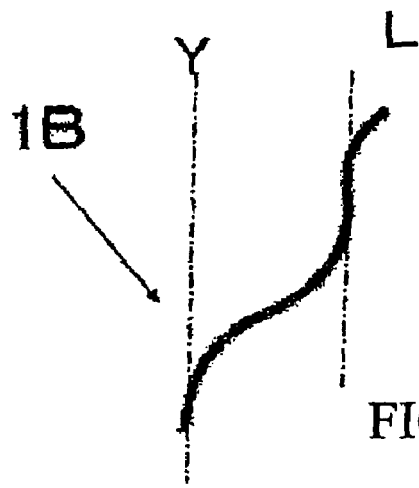
Figure 2C:
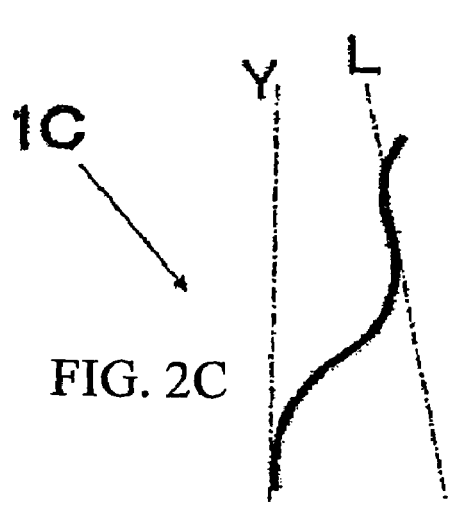
Figure 2D:
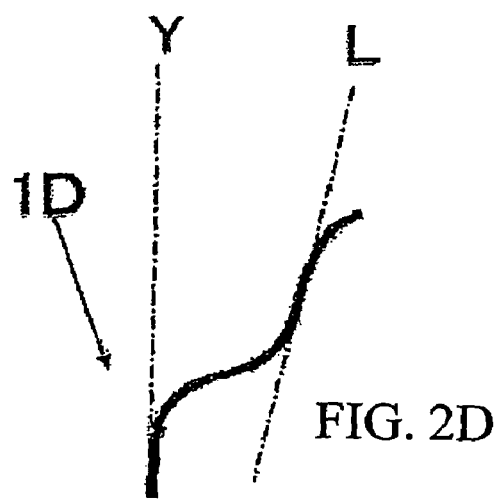

FIG. 2A schematically illustrates the guide wire shown in FIG. 1. FIGS. 2B-2D schematically illustrate other embodiments 1B, 1C, 1D of the guide wire.

With respect to the guide wire 1B, the direction L of the portion shifting from the second curve portion to the third curve portion is parallel (inclusive of approximately parallel to) the axis line Y. In the guide wire 1C, the direction L of the portion shifting from the second curve portion to the third curve portion is such that the distance between the line L and the axis line Y narrows toward the distal tip (i.e., the line Y approaches the axial line Y in the distal direction). In the guide wire 1D, similar to the guide wire 1A, the direction L of the portion shifting from the second curve portion to the third curve portion is such that the distance between the line L and the axis line Y increases toward the distal tip (i.e., the line Y diverges away from the axial line Y in the distal direction). The embodiment shown in FIG. 2D differs from the embodiment of the guide wire illustrated in FIG. 1 (FIG. 2A) in that the FIG. 2D embodiment of the guide wire is constructed such that the divergence between the line L and the axial line Y is greater towards the distal direction than in the embodiment shown in FIG. 1 (FIG. 2A).

Figure 3:
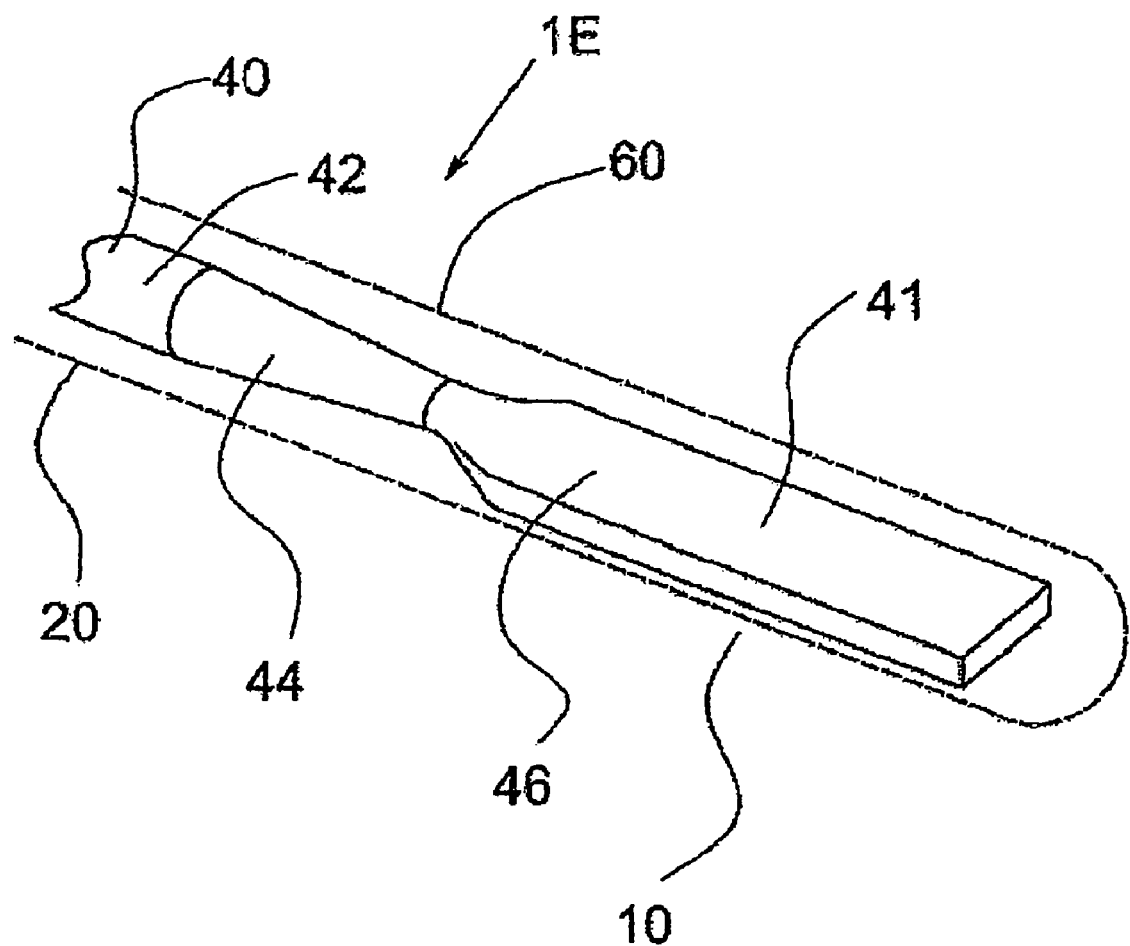
FIG. 3 is a perspective view showing the internal structure of a guide wire disclosed here.

FIG. 3 is a perspective view showing the internal structure of a guide wire disclosed here. To facilitate an understanding and illustration of the internal structure, the curve portions of the distal portion 10 are omitted in FIG. 3. The guide wire 1E shown in FIG. 3 includes a core wire 40 comprised of a core wire distal portion 41 and a coating portion 60 covering at least the core wire distal portion 41. The coating portion 60 is preferably composed of a resin. The core wire 40 comprises several portions. In the illustrated embodiment, the core wire 40 comprises a core wire main body portion 42, a taper portion 44 and the core wire distal portion 41. The material forming the core wire 40 can be NiTi alloy or stainless steel.

It is preferable for the core wire 40 to be composed of a superelastic alloy. The core wire main body portion 42 possesses a circular cross-sectional shape. The taper portion 44 is provided at the distal side of the core wire main body portion 42. The taper portion 44 is constructed such that its outer diameter becomes gradually smaller toward the distal tip. In the illustrated embodiment, the taper portion 44 tapers in outer diameter at a constant rate, though it is also possible to employ a configuration in which the taper angle changes at a portion of the taper portion. For example, a configuration can be employed in which the taper angle on the proximal side is larger than the taper angle on the distal side. Also, it is possible to employ a structure in which the taper angle on the proximal side is smaller than the taper angle on the distal side.

The core wire distal portion 41 is provided on the distal side of the taper portion 44. The core wire distal portion 41 includes a flat portion 46. The flat portion 46 has a width and thickness, with the width being larger than the thickness. With the illustrated configuration, the flat portion 46 can be bent in the thickness direction more easily. It is also possible for the core wire distal portion 41 to include an outer diameter uniform portion (a portion of uniform or constant outer diameter) on the distal side of the taper portion 44. In this case, a transition portion can be located on the distal side of the outer diameter uniform portion, with the flat portion 46 following. The transition portion provides a transitions from the outer diameter uniform portion to the flat portion. The cross-sectional area of the core wire main body portion 42 is larger than the cross-sectional area of the core wire distal portion 41. It is preferable for the flat portion 46 to be superelastic. In a load-distortion curve, the elastic modulus in the elastic region of the flat portion 46 is preferably smaller than the elastic modulus in the elastic region of the core wire main body portion 42. Based on such a construction, it is possible to impart flexibility even if the thickness of the flat portion 46 is not extremely small.

The coating portion 60 covering the core wire distal portion 41 is composed of a resin such as polyurethane or the like. In this disclosed embodiment, the coating portion 60 covers the core wire distal portion 41, the core wire main body portion 42 and the taper portion 44. However, it is also possible to utilize the cover portion 60 so that it covers only the core wire distal portion 41. In addition, it is also possible for the coating portion 60 to cover only the core wire distal portion 41 and the taper portion 44.

Figure 4:
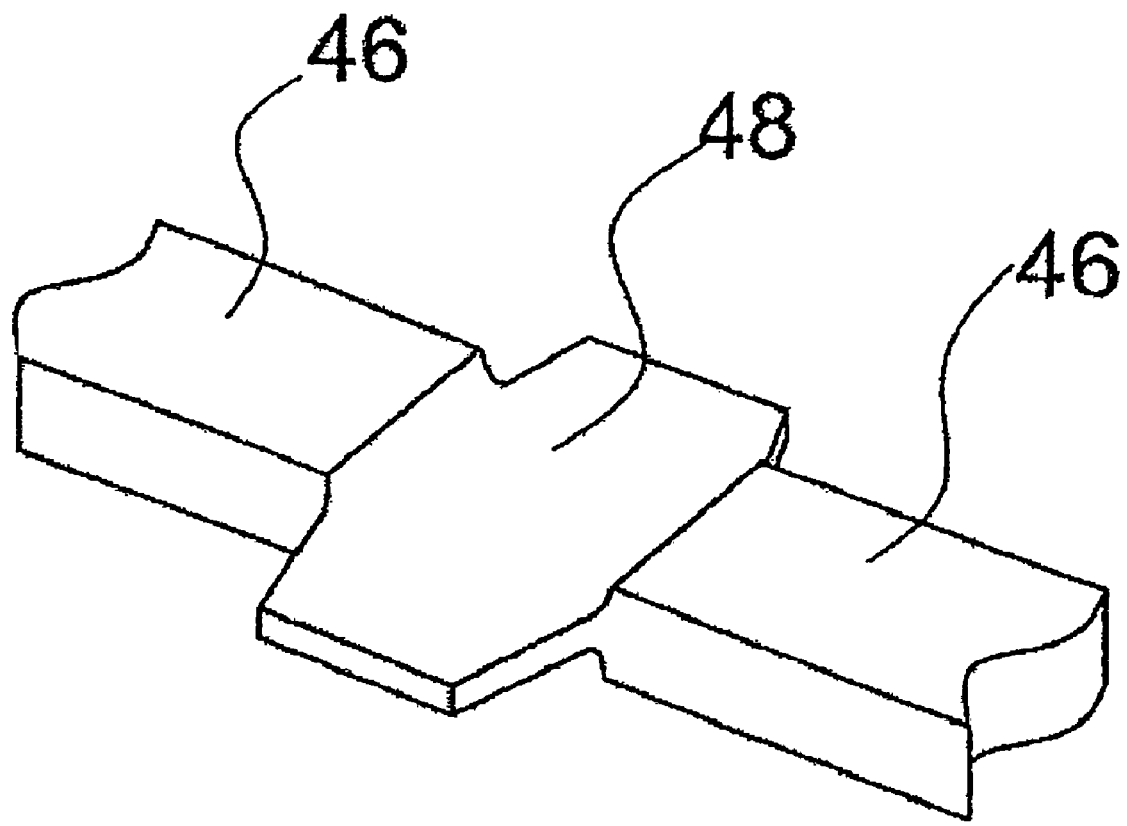
FIG. 4 is a perspective enlarged view showing a portion of the internal structure of the guide wire depicted in FIG. 3.

The flat portion 46 of the core wire distal portion 41 can also be provided with an elastic portion. Referring to FIG. 4, one way of accomplishing this is to provide an elastic portion 48 thinner than the flat portion 46 at an intermediate part of the flat portion 46. The width of the elastic portion 48 is preferably wider (greater) than the width of the flat portion 46. To help maintain the strength of the elastic portion 48, it is preferable to employ a structure in which the cross-sectional area of the flat portion 46 and the cross-sectional area of the elastic portion 48 are equal (inclusive of approximately equal). It is also possible to employ a structure in which the width of the elastic portion 48 is the same as the width of the flat portion 46 by making the thickness of the elastic portion 48 thinner than the thickness of the flat portion 46. For another example of the elastic portion, it is possible to provide the elastic portion by changing the material property using thermal treatment or the like. As mentioned, the curve portions of the distal portion 10 of the guide wire 1E are not specifically illustrated in FIG. 3 to help facilitate the illustration of the internal structure. However, it is to be understood that the guide wire includes curve portions as discussed above, and the guide wire 1E can possess any of the shapes associated with the guide wires 1A, 1B, 1C and 1D.

Figure 5:
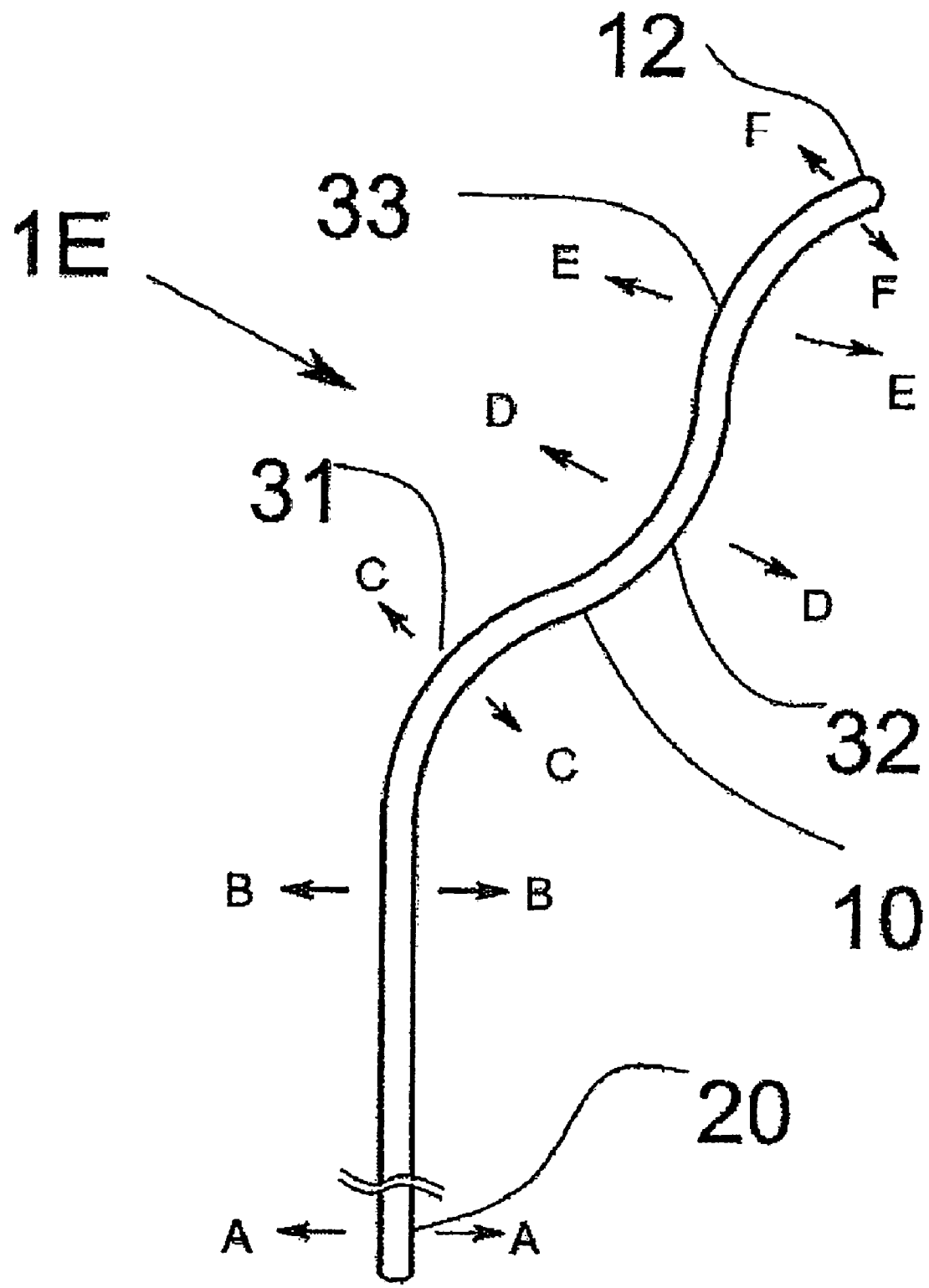
FIG. 5 is a partially enlarged view of another embodiment of a guide wire disclosed here.

FIG. 5 illustrates, in a partially enlarged manner, another embodiment of a guide wire disclosed here. The guide wire 1F can be provided with the structure shown in FIG. 3 and the shape of the guide wire 1A is comprised of the distal portion 10 and the main body portion 20. The distal portion 10 is provided with the first curve portion 31, the second curve portion 32 and the third curve portion 33. The second curve portion 32 is positioned on the distal side of the first curve portion 31, and is curved in a direction opposite the direction of curvature of the first curve portion 31. The third curve portion 33 is positioned on the distal side of the second curve portion 32 and is curved in a direction opposite the direction of curvature of the second curve portion 32. The first curve portion 31 has a higher (greater) flexibility compared with the main body portion 20. The second curve portion 32 has a higher (greater) flexibility compared with the first curve portion 31. The third curve portion 33 has the same flexibility compared with the second curve portion 32, though it is also possible for the third curve portion 33 to have a higher (greater) flexibility than the second curve portion 32.

FIGS. 6A-6F illustrate cross-sectional views (perpendicular to the axis of the guide wire 1E) of the guide wire shown in FIG. 5 taken along the correspondingly lettered section lines noted in FIG. 5.

Figures 6A, 6B:
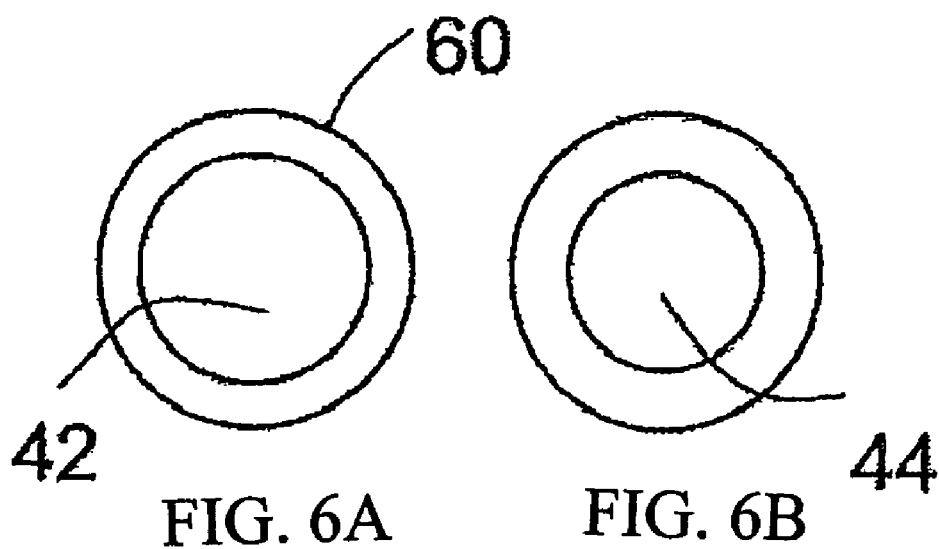
FIGS. 6A-6F are cross-sectional views of portions of the guide wire taken along the correspondingly lettered section lines shown in FIG. 5.

FIG. 6A shows the cross-sectional view of the main body portion 20 of the guide wire 1E. As illustrated, the guide wire 1E is composed of the core wire main body portion 42 of the core wire 40 and the coating portion 60 covering the periphery of the main body portion 42 in a concentric manner. The core wire main body portion 42 and the coating portion both possess circular cross-sectional shapes.

FIG. 6B illustrates a cross-section through the section line B-B in FIG. 5 and represents the cross-section of a portion of the guide wire positioned on the proximal side of the first curve portion 31 and on the axis line of linear portion of the main body portion 20. The position of the cross-section B-B is taken at the taper portion 44 in the core wire 40. The cross-sectional area of the taper portion 44 of the core wire 40 is smaller than the cross-sectional area of the core wire main body portion 42 in FIG. 6A.

Figures 6C, 6D:
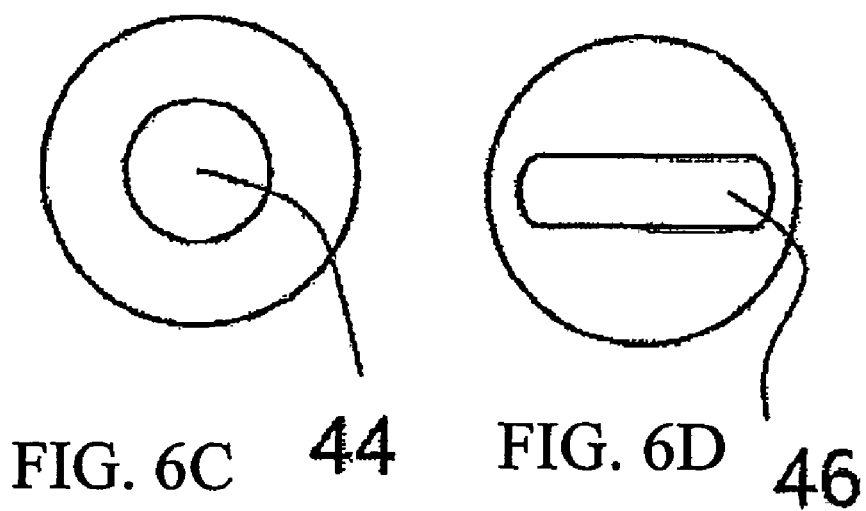

FIG. 6C illustrates a cross-section through the section line C-C in FIG. 5 and represents the cross-section at the vertex of the first curve portion 31 (point 51 in FIG. 1). The position of the FIG. 6C cross-section is at the taper portion 44 in the core wire 40, at a position on the distal side of the taper portion 44 relative to the cross-section B-B. The cross-sectional area of the taper portion 44 of the core wire 40 in the cross-sectional view of FIG. 6C-6C is smaller than the cross-section area of the taper portion 44 shown in FIG. 6B. The vertex of the first curve portion 31 is positioned between the start portion (proximal-most point) and the end portion (distal-most point) of the taper portion 44 of the core wire 40. The end portion of the taper portion 44 is positioned on the distal side of the vertex of the first curve portion 31. The first curve portion 31 is positioned at the taper portion 44 of the core wire 40 so that the first curve portion 31 and the taper portion 44 overlap one another or are coextensive with one another for at least a portion of their longitudinal extent. The core wire 40 in the first curve portion 31 is in the taper portion 44, so that the first curve portion 31 has a higher flexibility than the main body portion 20.

FIG. 6D illustrates a cross-section through the section line D-D in FIG. 5 and represents the cross-section of the guide wire at the vertex (point 52 in FIG. 1) of the second curve portion 32. The position of the cross-section shown in FIG. 6D is in the flat portion 46 in the core wire 40. The core wire 40 in the second curve portion 32 is in the flat portion 46, and so the second curve portion 32 has a higher flexibility than the first curve portion 31. The cross-sectional area of the flat portion 46 in the second curve portion 32 is smaller than the cross-sectional area of the taper portion 44 in the first curve portion 31. The thickness of the flat portion 46 is smaller than the outer diameter of the taper portion 44 in the first curve portion 31. Therefore, the second curve portion 32 has a higher flexibility than the first curve portion 31. With this construction, the guide wire is not as likely to erroneously enter into a side-branch even if the most distal tip 12 of the guide wire 1E gets into a side-branch caused by a fact that the flexible second curve portion 32 is bent more before the most distal tip 12 is further inserted and the guide wire advances in the main blood vessel with the second curve portion 32 being set at the forefront.

Figures 6E, 6F:
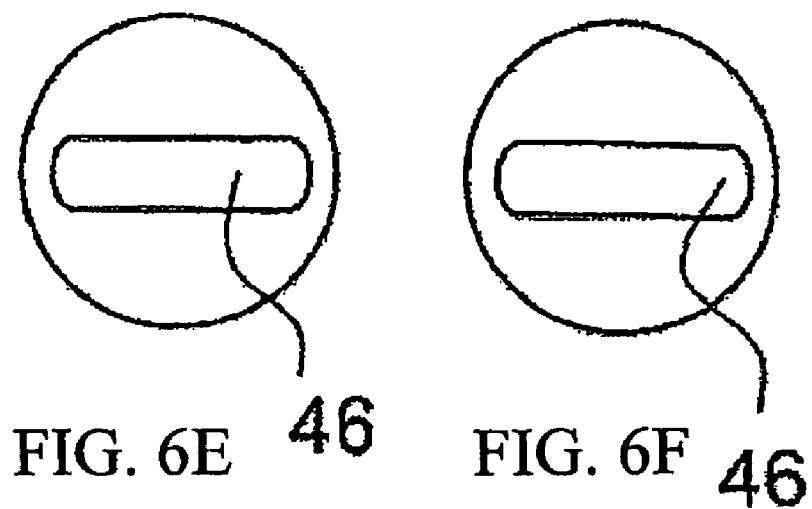

FIG. 6E illustrates a cross-section through the section line E-E in FIG. 5 and represents the cross-section of the guide wire at the vertex (point 53 in FIG. 1) of the third curve portion 33. The position of the cross-section shown in FIG. 6E is at the flat portion 46 in the core wire 40. The core wire 40 at the third curve portion 33 is in the same flat portion 46 as the second curve portion 32, so that the flexibility of the third curve portion 33 is the same as the flexibility of the second curve portion 32.

FIG. 6F illustrates a cross-section of the guide wire through the section line F-F in FIG. 5 and represents the cross-section of the guide wire at the most distal tip 12. The position of the section line F-F is at the flat portion 46 in the core wire 40. The core wire 40 at the most distal tip 12 is in the same flat portion 46 as the second curve portion 32 and the third curve portion 33, and so the flexibility of the third curve portion 33 is the same as the flexibility of the second curve portion 32 and the third curve portion 33.

FIGS. 7A-7F illustrate cross-sectional views (perpendicular to the axis of the guide wire) of another embodiment of the guide wire, taken at positions corresponding to the correspondingly lettered section lines noted in FIG. 5.

FIGS. 7A-7F show another embodiment of the guide wire in which the cross-sectional views shown in FIGS. 7A, 7D, 7E and 7F are the same as those shown in FIGS. 6A, 6D, 6E and 6F, respectively, but the cross-sectional area of the core wire 40 in FIG. 7B (corresponding to the position of the section line B-B in FIG. 5) is smaller than the cross-sectional area of the core wire 40 in the FIG. 6B cross-section, and the core wire 40 in FIG. 7C (corresponding to the position of the section line C-C in FIG. 5) is positioned at the flat portion 46. The cross-sectional area of the flat portion 46 shown in the FIG. 7C cross-section is smaller than the cross-sectional area of the taper portion 44 in the FIG. 7B cross-section. The core wire 40 in the first curve portion 31 is in the flat portion 46, and so the first curve portion 31 has higher flexibility (i.e., is more flexible) than the main body portion 20.

Figures 8A, 8B:
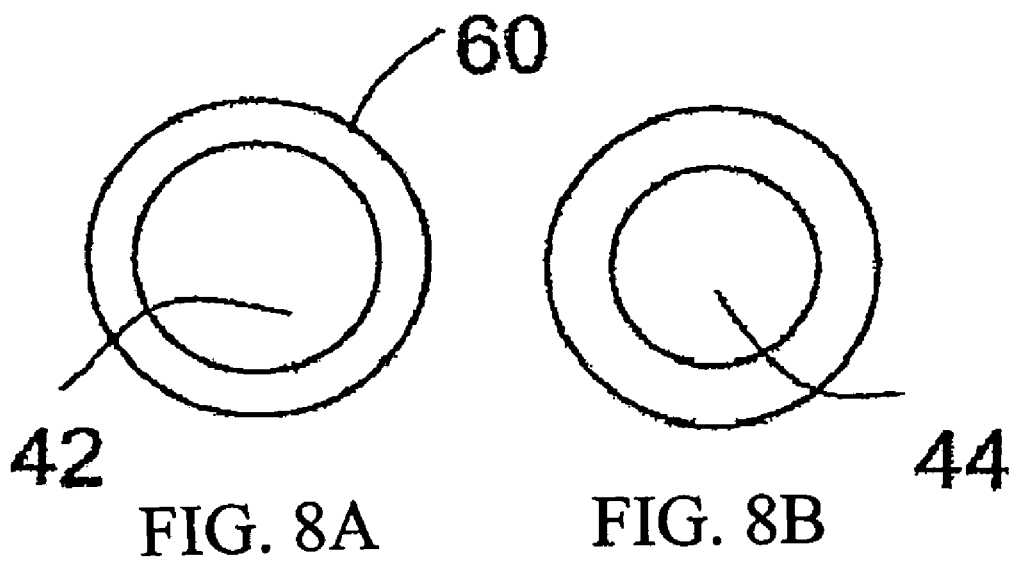
FIGS. 8A-8F are cross-sectional views of portions of another embodiment of a guide wire taken along section lines corresponding in position to the correspondingly lettered section lines in FIG. 5.
Figures 8C, 8D:
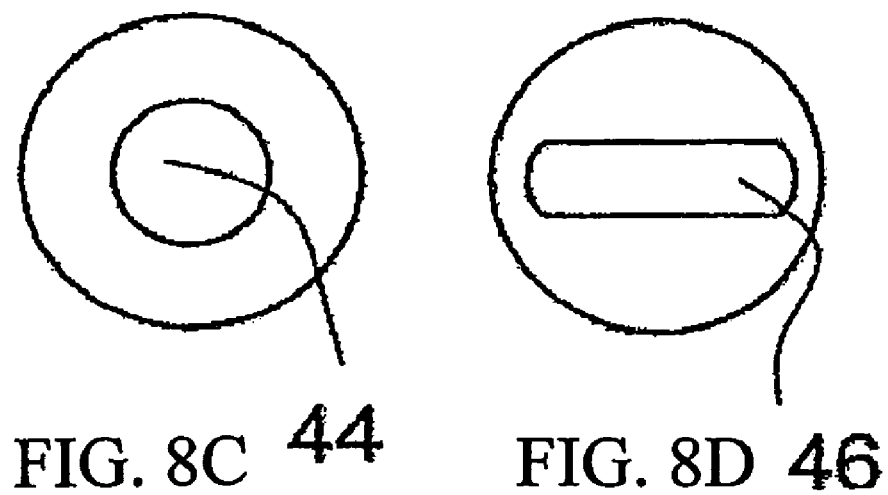
Figures 8E, 8F:
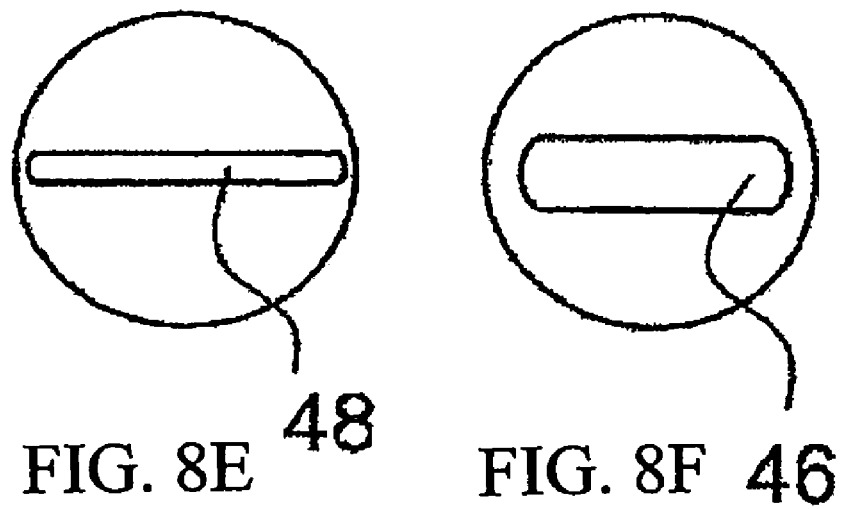

FIGS. 8A-8F show another embodiment of the guide wire in which the cross-sectional views of the guide wire shown in FIGS. 8A, 8B. 8C, 8D and 8F are the same as those shown in FIGS. 6A, 6B, 6C, 6D and 6F, respectively, but the cross-sectional view shown in FIG. 8E differs with respect to the elastic portion 48 of the core wire 40. As shown in FIG. 8E, the elastic portion 48 is thinner than the flat portion 46. The width of the elastic portion 48 is also wider than the width of the flat portion 46. Consequently, the third curve portion 33 has a higher flexibility than the second curve portion 32.

Figure 9A:
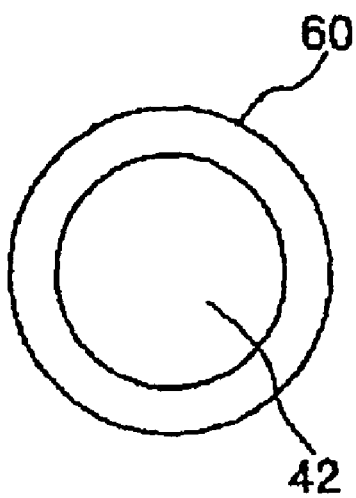
FIGS. 9A-9F are cross-sectional views of portions of another embodiment of a guide wire taken along section lines corresponding in position to the correspondingly lettered section lines in FIG. 5.
Figure 9B:
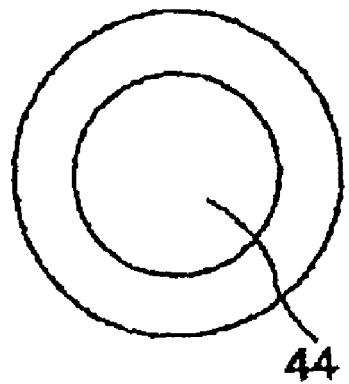
Figure 9C:
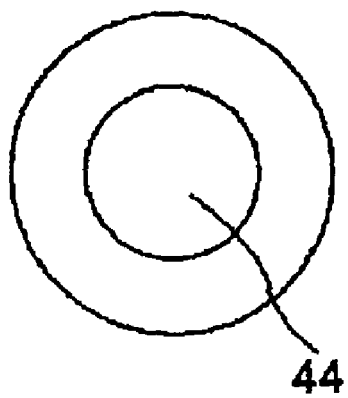
Figure 9D:
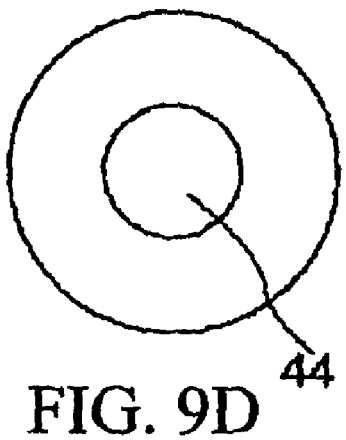
Figure 9E:
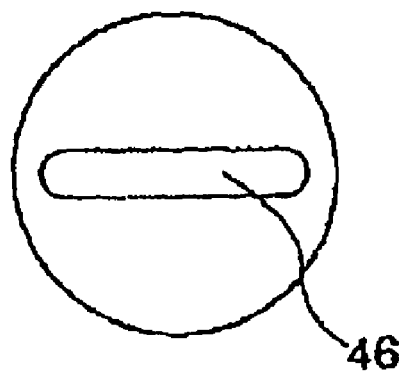
Figure 9F:
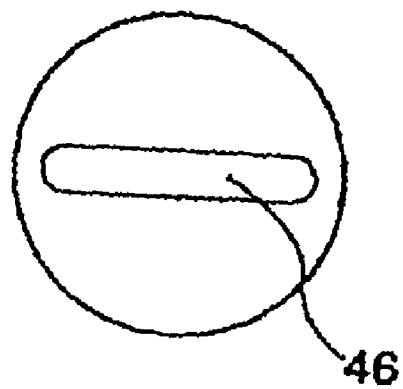

FIGS. 9A-9F illustrate another embodiment of the guide wire in which the cross-sectional views of the guide wire shown in FIGS. 9A and 9B are the same as those shown in FIGS. 6A and 6B, respectively. The cross-sectional area of the taper portion 44 shown in FIG. 9C (taken at a position on the guide wire corresponding to the section line C-C in FIG. 5) is larger than the cross-sectional area of the taper portion 44 shown in FIG. 6C. Also, the cross-sectional area of the taper portion 44 shown in FIG. 9D (taken at a position on the guide wire corresponding to the section line D-D in FIG. 5) is smaller than the cross-sectional area of the taper portion 44 shown in FIG. 6D. With this construction, the second curve portion 32 has a higher flexibility than the first curve portion 31. The core wire 40 in FIG. 9E and FIG. 9F is in the flat portion 46 of the core wire. The thicknesses of the flat portions 46 in these sections shown in FIGS. 9E and 9F represent are the same and are smaller than the thickness of the flat portion 46 in FIG. 6E and FIG. 6F. By virtue of this construction, the third curve portion 33 possesses a higher flexibility than the first curve portion 31 and the second curve portion 32. Thus, even if the most distal tip 12 of the guide wire moves into a branch, it turns around at the third curve portion 33 and advances in the main blood vessel, and so erroneous-entering into a branch is inhibited or prevented.

Figure 10:
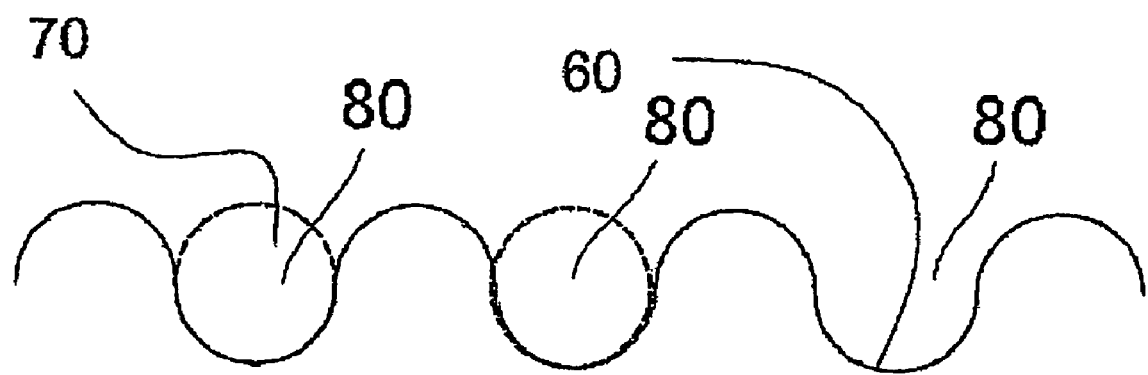
FIG. 10 is a cross-sectional view of a guide wire according to another embodiment disclosed here.

FIG. 10 is a cross-sectional view of another embodiment of a guide wire disclosed here.

FIG. 10 shows an embodiment of the guide wire for softening (making more flexible) the curve portion. As shown in FIG. 10, the guide wire is provided with a groove 80 in a direction perpendicular (inclusive of substantially perpendicular) to the axis on the surface (outer surface) of the coating portion 60 of at least the inner side of the curve portion. The groove 80 possess a spiral shape and is provided on the outer surface of the curve portion. For example, the groove 80 is provided on the entire outer circumference of the surface of the coating portion 60 of the second curve portion 32 and the third curve portion 33 in FIG. 1, FIG. 2 or FIG. 5. The groove 80 is provided only on the surface of the coating portion 60 of the curve portion. As shown in FIG. 10, the horizontal cross-section of the groove 80 is such that the vertical cross-section shape of the outer surface (outer circumference face) of the coating portion 60 possesses a wave shape. It is possible to obtain the wave shaped groove 80 by, for example, winding a wire 70 on the coating portion 60 with a gap for the outer diameter of the wire 70 and by heating it. More specifically, and by way of example, the wire 70 may be wound with tension on the coating portion 60 which has a smooth and non-groove surface. The wire 70 may be wound such that each turn (winding) of the wound wire 70 is spaced apart from the adjacent turn (winding) by a distance that is the same as the outer diameter of the wire 70 in order to ultimately make the wave shaped groove 80. Thereafter, the coating portion 60 with the wound wire 70 may be heated to soften the coating portion. The wire 70 wound on the coating portion 60 is able to dig into the softened coating portion 60 as shown in FIG. 10. Finally the wire 70 may then be removed from the coating portion 60, with the result being the grooved surface.

It is also possible for the groove 80 to be in a loop shape other than in a spiral shape. Also, it is possible to employ a slit shape instead of a groove 80. The groove 80 can be provided only on the front face of the coating portion 60 on the inner side of the curve portion, for example, the second curve portion 32 and the third curve portion 33 in FIG. 1, FIG. 2 or FIG. 5.

In the present embodiments, the flexibility of the curve portion is increased by providing a groove 80 or a slit almost perpendicular to the axial direction on the front face of the coating portion 60 at least on the inner side of the curve portion, so that the curve portion can be more easily bent.

Aforesaid illustrative embodiment for softening the curve portion can be used in connection with each of the embodiments of the guide wire described above.

Softening the curve portion(s) of the guide wire to make the curve portion(s) more flexible can be also realized by thermally-treating the core wire at the curve portion and by converting or transforming it to a material having a higher flexibility compared with other portions.

It is possible to use the guide wires disclosed here to introduce a medical device such as a catheter, a sheath or the like from a radial, a brachial and a femoral to an aimed region such as a chest region, an abdominal region or the like, and the use of the guide wires described and illustrated here is not limited to being used in the noted contexts such as where the guide wire-introduced region is a radial, brachial or femoral where the guide wire might otherwise have a tendency to become stuck during use.

The description which follows describes concrete examples of guide wires produced according to the disclosure herein.

1. Manufacturing of Guide Wire

Inventive Example

Figure 11:
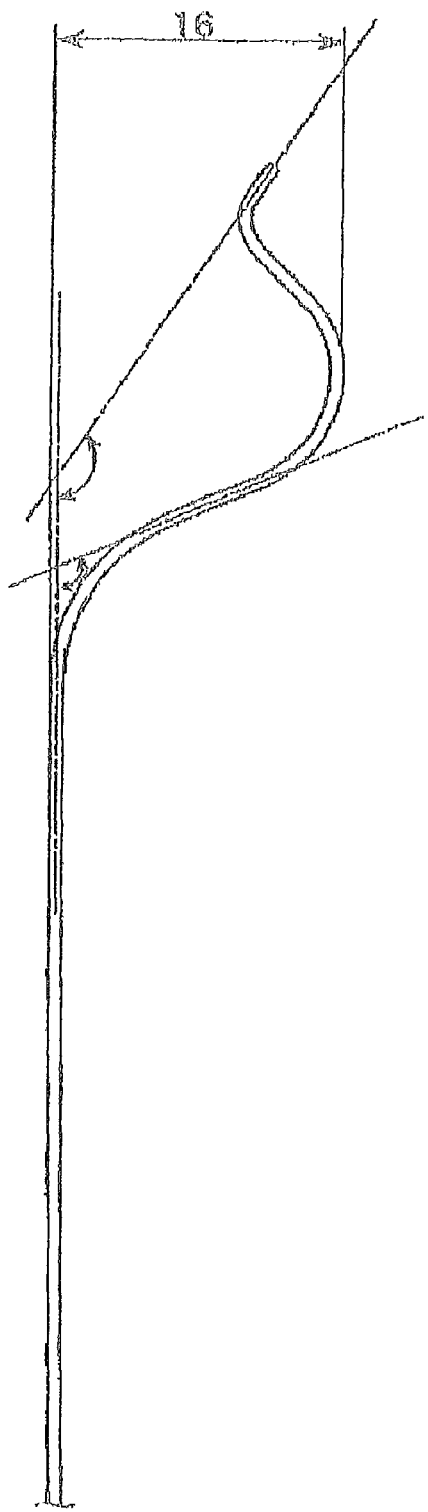
FIG. 11 is a plan view of a specific configuration of the guide wire shown in FIG. 1.

A guide wire shown in FIG. 11 was manufactured so that the guide wire has an outer diameter of 0.89 mm and a full length of 1500 mm. The core wire composing the guide wire was made of Ni—Ti and the coating portion was made of polyurethane. Also, with respect to the flat portion, the length of the flat portion was 4 mm, the width of the flat portion 0.23 mm and the thickness of the flat portion was 0.03 mm. Also, the guide wire was fabricated so that the distance $\overline{D}$ was about 8.5 mm and the distance $\overline{E}$ was about 13.5 mm.

Comparative Example 1

Figure 12:
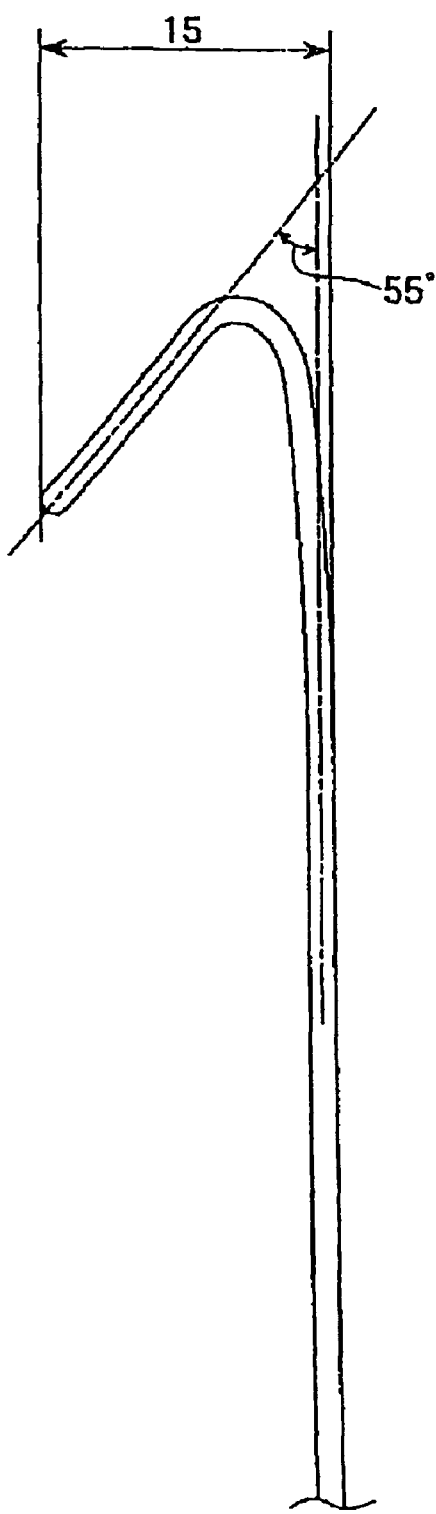
FIG. 12 is a plan view of a specific configuration of comparative example 1 of a guide wire used for testing and evaluation.

A guide wire shown in FIG. 12 was manufactured. The outer diameter, the full length and the constituent material of this guide wire were similar to those discussed above in the inventive example.

Comparative Example 2

Figure 13:
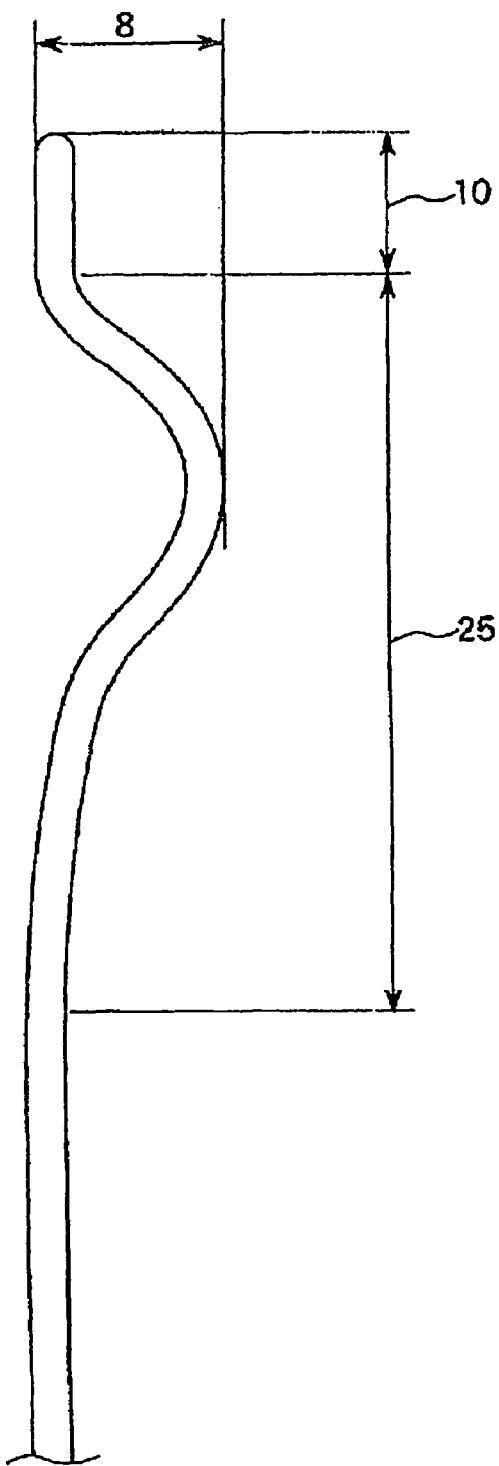
FIG. 13 is a plan view of a specific configuration of comparative example 2 of a guide wire used for testing and evaluation.

A guide wire shown in FIG. 13 was manufactured. The outer diameter, the full length and the constituent material of the guide wire were similar to those discussed above in the inventive example.

Comparative Example 3

Figure 14:
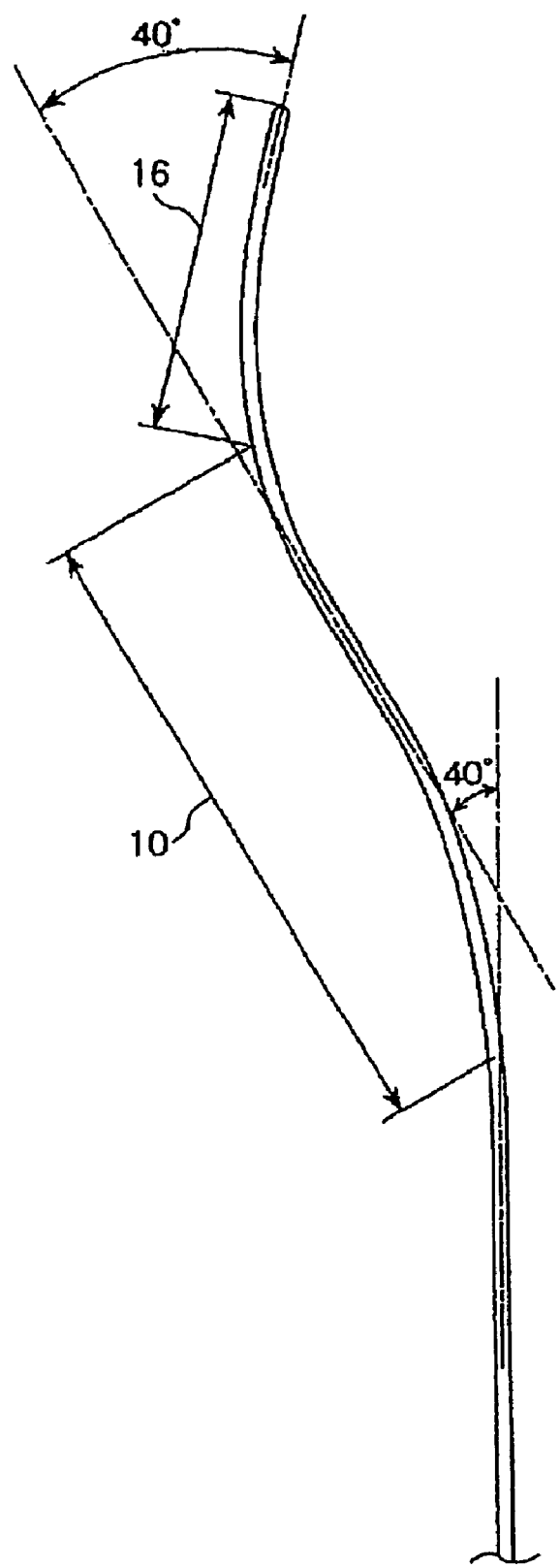
FIG. 14 is a plan view of a specific configuration of comparative example 3 of a guide wire used for testing and evaluation.

A guide wire shown in FIG. 14 was manufactured. The outer diameter, the full length and the constituent material of the guide wire were similar to those discussed above in the inventive example.

Comparative Example 4

Figure 15:
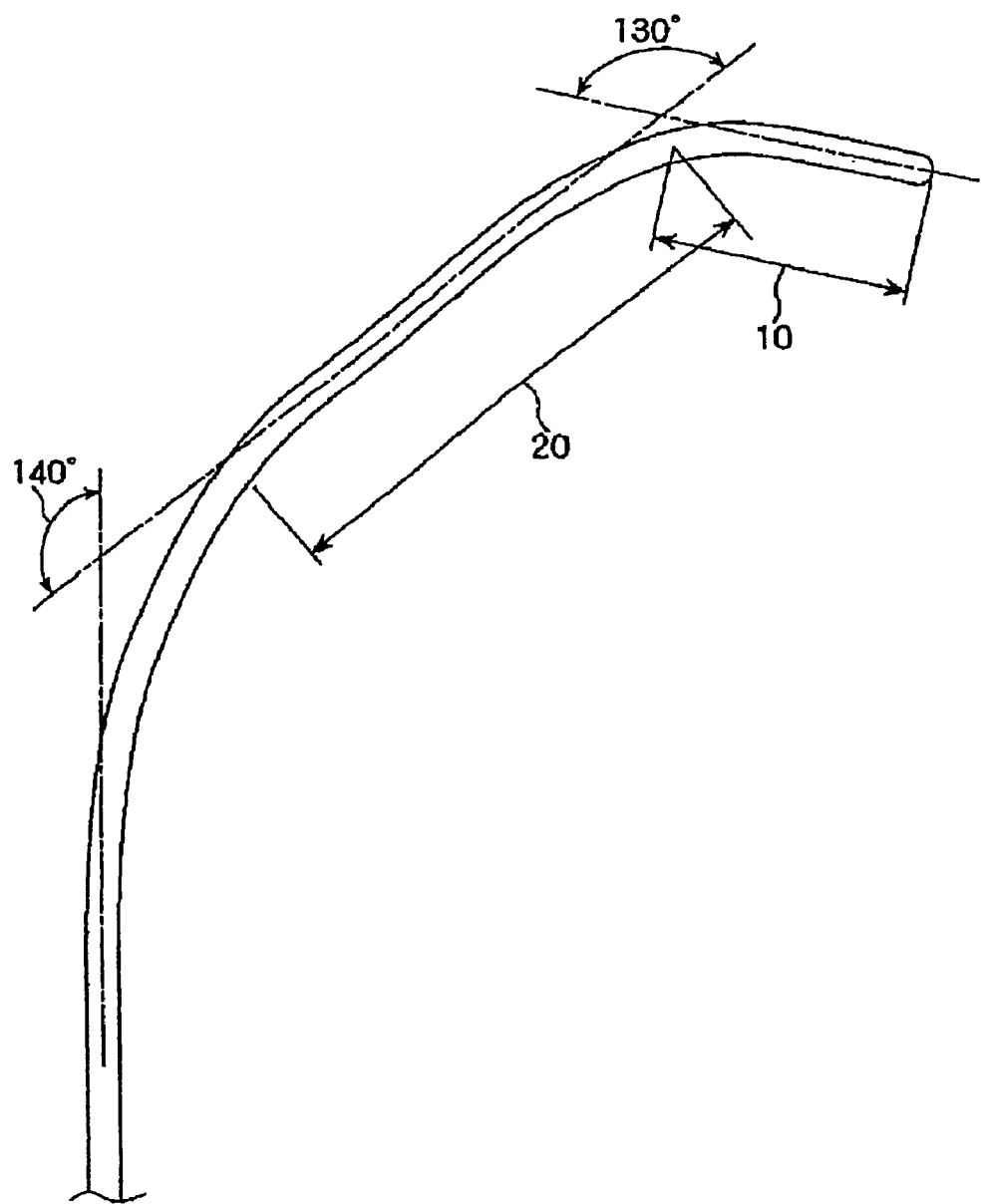
FIG. 15 is a plan view of a specific configuration of comparative example 4 of a guide wire used for testing and evaluation.

A guide wire shown in FIG. 15 was manufactured. The outer diameter, the full length and the constituent material of the guide wire were similar to those discussed above in the inventive example.

Comparative Example 5

Figure 16:
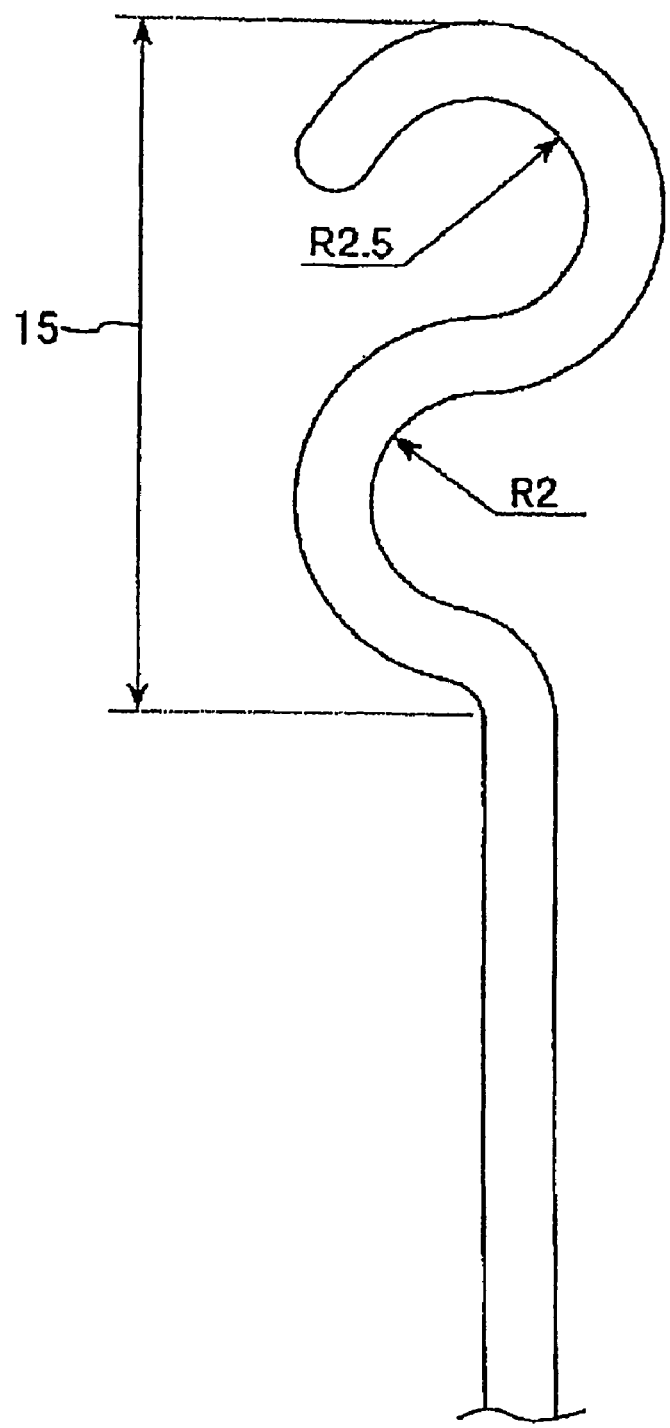
FIG. 16 is a plan view of a specific configuration of comparative example 5 of a guide wire used for testing and evaluation.

A guide wire shown in FIG. 16 was manufactured. The outer diameter, the full length and the constituent material of the guide wire were similar to those discussed above in the inventive example.

In FIG. 11 to FIG. 16, the units of length are always "mm".

2. Evaluation 2.1 Evaluation Using the Evaluation Tool Shown in FIG. 17

Figure 17:
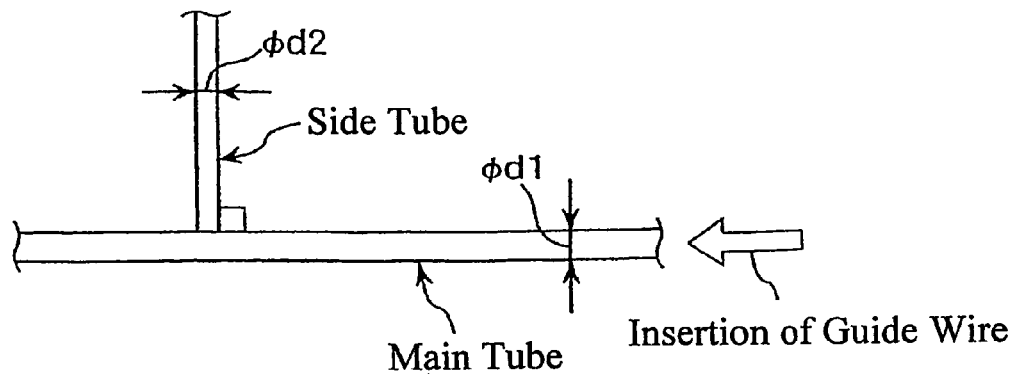
FIG. 17 is a schematic illustration of an evaluation tool used to test and evaluate the guide wires shown in FIGS. 11-16.

With respect to the guide wires obtained by the inventive example and the respective comparative examples, evaluations were executed using the evaluation tool shown in FIG. 17. The evaluation tube includes a "main tube" and a "side tube." This evaluation tool is a tool based on the assumption of a straight-line shaped blood vessel and a side-branch branching from the blood vessel at a point along the length of the blood vessel. In the FIG. 17 illustration, the "main tube" corresponds to the "straight-line shaped blood vessel" and the "side tube" corresponds to the "side-branch". The main tube and the side tube are both made of polypropylene.

The evaluation was executed by preparing evaluation tools 1a to 5a in which the inner diameters φd1 of the main tubes and the inner diameters φd2 of the side tubes are respectively different (as noted in the table below). The testing involved inserting the guide wire from the distal side thereof into the main tube of each evaluation tool five times. Evaluation was performed to determine whether or not the distal portion of the guide wire intrudes into the side tube at least once within those five times for each evaluation tool. The evaluation criteria were as follows.

○: means a case in which the distal portion of the guide wire did not intrude into the side tube at all (i.e., did not intrude into the side tube of the respective evaluation tool in any of the five insertions).

x: means a case in which the distal portion of the guide wire intruded into the side tube at least once.

The evaluation results are shown in Table 1.

TABLE 1

| Guide Wire | Evaluation Tool 1a<br>φd1: 4 mm<br>φd2: 1 mm | Evaluation Tool 2a<br>φd1: 4 mm<br>φd2: 2 mm | Evaluation Tool 3a<br>φd1: 5 mm<br>φd2: 2 mm | Evaluation Tool 4a<br>φd1: 6 mm<br>φd2: 3 mm | Evaluation Tool 5a<br>φd1: 8 mm<br>φd2: 8 mm |
|---|---|---|---|---|---|
| Inventive Example 1 | ○ | ○ | ○ | ○ | ○ |
| Comparative Example 1 | ○ | ○ | ○ | X | X |
| Comparative Example 2 | ○ | X | ○ | ○ | ○ |
| Comparative Example 3 | ○ | X | X | X | ○ |
| Comparative Example 4 | ○ | X | X | X | X |
| Comparative Example 5 | ○ | ○ | ○ | ○ | ○ |

Figure 18:
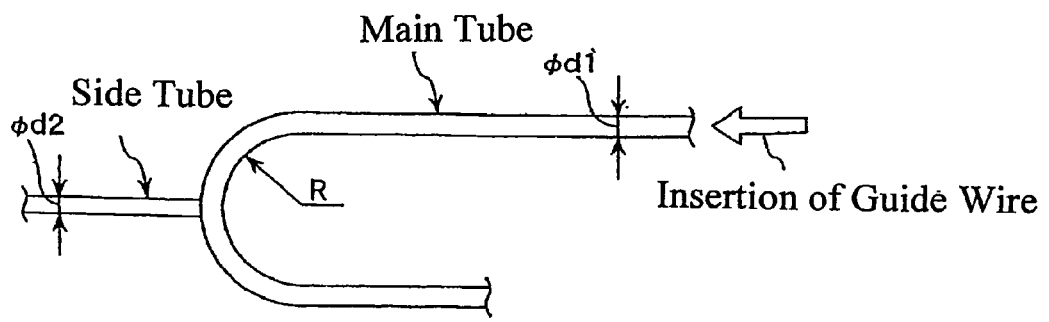
FIG. 18 is a schematic illustration of another evaluation tool used to test and evaluate the guide wires shown in FIGS. 11-16.

2.2 Evaluation Using the Evaluation Tool Shown in FIG. 18

With respect to the guide wires obtained by the inventive example and the respective comparative examples, evaluations were executed using the evaluation tool shown in FIG. 18. This evaluation tool is a tool based on the assumption of a curved blood vessel (Ulnar Loop) and a side-branch branching from the central portion of the curve portion of the blood vessel toward the outside. In the FIG. 18 illustration of the evaluation tool, the "main tube" corresponds to the "curved blood vessel" and "side tube" corresponds to the "side-branch". The main tube and the side tube are both made of polypropylene.

Here, testing and evaluation similar to that described above were performed by preparing five evaluation tools 1b to 5b in which the inner diameters φd1 of the main tubes and the inner diameters xφd2 of the side tubes are respectively different as noted in the table below.

The evaluation results using evaluation tools 1a-5a are shown in Table 2.

TABLE 2

| Guide Wire | Evaluation Tool 1a<br>φd1: 4 mm<br>φd2: 1 mm<br>R: 10 mm | Evaluation Tool 2a<br>φd1: 4 mm<br>φd2: 2 mm<br>R: 10 mm | Evaluation Tool 3a<br>φd1: 5 mm<br>φd2: 2 mm<br>R: 10 mm | Evaluation Tool 4a<br>φd1: 6 mm<br>φd2: 3 mm<br>R: 10 mm | Evaluation Tool 5a<br>φd1: 8 mm<br>φd2: 8 mm<br>R: 20 mm |
|---|---|---|---|---|---|
| Inventive Example 1 | ○ | ○ | ○ | ○ | ○ |
| Comparative Example 1 | ○ | ○ | ○ | ○ | X |
| Comparative Example 2 | ○ | X | ○ | ○ | X |
| Comparative Example 3 | ○ | X | X | X | X |
| Comparative Example 4 | ○ | ○ | ○ | ○ | X |
| Comparative Example 5 | ○ | ○ | ○ | ○ | X |

As clear from Table 1 and Table 2, with respect to the guide wire obtained by the inventive example, the distal portion of the guide wire did not intrude into the side tube at all in any of the evaluation tools.

On the other hand, with respect to the guide wires obtained by respective comparative examples, each of the guide wires experienced at least one instance in which the distal portion of the guide wire intruded into the side tube.

Also, the guide wires shown in FIG. 2 and FIG. 5 to FIG. 10 were manufactured, and testing and evaluations similar to those of the aforesaid inventive example were executed with respect to them. Similar results as those of the aforesaid inventive example were obtained also with respect to the guide wires shown in FIGS. 2 and 5-10.

2.3 Evaluation by Using Catheter

With respect to the guide wires obtained by the inventive example and the comparative examples, evaluations were also carried out using a catheter. This catheter was a catheter including a tube-shaped catheter main body having elasticity and a hub installed at the proximal portion of the aforesaid catheter main body. The hub was a hub having a cylindrical shape and communicates with the catheter main body. Also, the inner diameter of the catheter main body was φ1.05 mm and the inner diameter of the hub entrance port was φ4 mm.

Here, insertion of the guide wire from the distal side thereof with respect to the hub was attempted five times and an evaluation was conducted to determine whether or not the distal portion of the guide wire was inserted into the hub at least once within those five times. The evaluation criteria were as follows.

○: means a case in which the distal portion of the guide wire could be inserted all five times x: means a case in which the distal portion of the guide wire could not be inserted at least once The evaluation results are shown in Table 3 below.

TABLE 3

| Guide Wire | Catheter<br>Inner Diameter of Catheter Main Body: φ1.05 mm<br>Inner Diameter of Hub Input Port: φ4 mm |
|---|---|
| Inventive Example 1 | ○ |
| Comparative | ○ |

TABLE 3-continued

| Guide Wire | Catheter<br>Inner Diameter of Catheter Main Body: φ1.05 mm<br>Inner Diameter of Hub Input Port: φ4 mm |
|---|---|
| Example 1 | |
| Comparative Example 2 | ◯ |
| Comparative Example 3 | ◯ |
| Comparative Example 4 | ◯ |
| Comparative Example 5 | X |

As clear from Table 3, with respect to the guide wire according to the inventive example, the distal portion of the guide wire could be inserted into the hub all five times.

On the other hand, with respect to the guide wires obtained by respective comparative examples, there occurred a case in which the distal portion of the guide wire could not be inserted into the hub at least once.

Also, the guide wires shown in FIG. 2 and FIG. 5 to FIG. 10 were manufactured, and testing and evaluations similar to those of the aforesaid inventive example were executed with respect to them. Similar results as those shown in Table 3 for the aforesaid inventive example were obtained also with respect to the guide wires shown in FIGS. 2 and 5-10.

The guide wire disclosed here is a guide wire which includes a distal portion and a main body portion and which is provided with a first curve portion; a second curve portion on the distal side of the first curve portion and curved in a direction opposite the direction of curvature of the first curve portion, and a third curve portion on the distal side of the second curve portion and curved in a direction opposite the direction of curvature of the second curve portion. A line contacting both the first curve portion and the third curve portion forms an angle with respect to an axial line of the main body portion. The guide wire possesses quite good steerability characteristics when the guide wire is operated.

The principles, embodiments and modes of operation of the guide wire have been described in the foregoing specification, but the invention which is intended to be protected is not to be construed as limited to the particular embodiments disclosed. The embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
an elongated member comprised of a straight main body portion and a curved distal portion positioned on a distal side of the straight main body portion;
the straight main body portion being straight and possessing an axis;
the curved distal portion of the elongated member comprising a first curve portion, a second curve portion and a third curve portion, each of the first, second and third curve portions having a shape that is curved in a state of the guide wire in which an external force is not applied to the guide wire;
the first curve portion being more flexible than the main body portion;
the first curve portion immediately following a distal end of the straight main body portion and curving in a direction of curvature;
the second curve portion being positioned distally of the first curve portion;
the second curve portion curving in a direction of curvature that is opposite the direction of curvature of the first curve portion;
the second curve portion being more flexible than the first curve portion, the second curve portion possessing a vertex;
the third curve portion being positioned distally of the second curve portion, the third curve portion possessing a vertex;
the third curve portion curving in a direction opposite the direction of curvature of the second curve portion;
wherein a line contacting both the first curve portion and the third curve portion forms an obtuse angle with respect to the axis of the main body portion;
the line contacting both the first curve portion and the third curve portion is a first line, a second line parallel to the first line contacts the second curve portion, and the elongated member possesses a distal most tip positioned between the first and second lines, wherein the first line, the second line, and the axis of the straight main body portion all extend along a common plane; and
the entirety of the guide wire between the vertex of the second curve portion and the vertex of the third curve portion is positioned between the first and second lines.

2. The guide wire according to claim 1, wherein the first and third curve portions each comprise a vertex, and said line contacts the vertex of both the first curve portion and the third curve portion.

3. The guide wire according to claim 1, wherein the elongated member comprises a core wire and a resin coating portion covering at least a distal portion of the core wire, the distal portion of the core wire covered by the coating portion comprising a flat portion.

4. A guide wire comprising:
an elongated member comprised of a main body portion and a distal portion positioned on a distal side of the main body portion;
the elongated member comprising a core wire and a resin coating portion covering the core wire and contacting the core wire;
the main body portion possessing an axis;
the elongated member comprising a first curve portion curving in a direction of curvature, a second curve portion possessing a vertex and a third curve portion possessing a vertex, each of the first, second and third curve portions having a shape that is curved in a state of the guide wire in which an external force is not applied to the guide wire;
the second curve portion being positioned on a distal side of the first curve portion;
the second curve portion curving in a direction of curvature that is opposite the direction of curvature of the first curve portion;
the third curve portion being positioned on a distal side of the second curve portion;
the third curve portion curving in a direction opposite the direction of curvature of the second curve portion;
wherein a line contacting both the first curve portion and the third curve portion forms an obtuse angle with respect to the axis of the main body portion;
the line contacting both the first curve portion and the third curve portion is a first line, a second line parallel to the first line contacts the second curve portion, and the elongated member possesses a distal most tip positioned between the first and second lines, wherein the first line, the second line, and the axis of the main body portion all extend along a common plane; and the entirety of the guide wire between the vertex of the second curve portion and the vertex of the third curve portion is positioned between the first and second lines.

5. The guide wire according to claim 4, wherein a portion of the elongated member shifting from the first curve portion to the second curve portion extends along a line forming a first angle with the axis of the main body portion, the elongated member possessing a distal most portion extending along a line forming a second angle with the axis of the main body portion, the first angle being greater than the second angle.

6. The guide wire according to claim 4, wherein the elongated member comprises a portion shifting from the second curve portion to the third curve portion that is parallel to the axis of the main body portion.

7. The guide wire according to claim 4, wherein the elongated member comprises a portion shifting from the second curve portion to the third curve portion that diverges relative to the axis of the main body portion in a direction towards a distal most end of the elongated member.

8. The guide wire according to claim 4, wherein the elongated member comprises a portion shifting from the second curve portion to the third curve portion, the portion converging relative to the axis of the main body portion in a direction towards a distal most end of the elongated member.

9. The guide wire according to claim 4, wherein the first curve portion has a higher flexibility than the main body portion and the second curve portion has a higher flexibility than the first curve portion.

10. The guide wire according to claim 4, wherein the elongated member comprises a core wire and a coating portion, the coating portion being comprised of a resin covering at least a distal portion of the core wire.

11. The guide wire according to claim 10, wherein the distal portion of the core wire covered by the coating portion includes a flat portion.

12. The guide wire according to claim 10, wherein the core wire at the third curve portion is a flat portion, and the third curve portion possesses a higher flexibility than the flexibility of the second curve portion.

13. A guide wire possessing an outermost surface and comprising:
an elongated member comprised of a main body portion having an axis, and a distal portion positioned on a distal side of the main body portion, the distal portion having a shape that is curved in a state of the guide wire in which an external force is not applied to the guide wire;
the elongated member comprising a core wire and a resin coating portion covering the core wire and contacting the core wire, and wherein the resin coating portion is the outermost surface of the guide wire;
a first curve portion provided at the distal portion of the elongated member, the first curve portion curving in a direction of curvature;
a second curve portion positioned distally of the first curve portion and curving in a direction of curvature that is opposite the direction of curvature of the first curve portion, the second curve portion possessing a vertex;
a third curve portion positioned distally of the second curve portion and curved in a direction opposite the direction of curvature of the second curve portion, the third curve portion possessing a vertex;

wherein the first curve portion possesses a higher flexibility than the main body portion, and the second curve portion possesses a higher flexibility than the first curve portion; and
a first line contacts both the first curve portion and the third curve portion, and intersects the axis of the main body portion, a second line parallel to the first line contacts the second curve portion, and the elongated member possessing a distal most tip positioned between the first and second lines, wherein the first line, the second line, and the axis of the main body portion all extend along a common plane; and
the entirety of the guide wire between the vertex of the second curve portion and the vertex of the third curve portion is positioned between the first and second lines.

14. The guide wire according to claim 13, wherein the third curve portion possesses a flexibility greater than or equal to the flexibility of the second curve portion.

15. The guide wire according to claim 13, wherein the core wire possesses a flat distal portion covered by the coating portion.

16. The guide wire according to claim 13, wherein the core wire at the third curve portion is a flat portion, and the third curve portion possesses a higher flexibility than the flexibility of the second curve portion.

17. A guide wire comprising:
an elongated member comprised of a straight main body portion and a curved distal portion positioned on a distal side of the straight main body portion;
the straight main body portion being straight and possessing an axis;
the curved distal portion of the elongated member comprising a first curve portion, a second curve portion and a third curve portion; each of the first, second and third curve portions having a shape that is curved in a state of the guide wire in which an external force is not applied to the guide wire;
the first curve portion immediately following a distal end of the straight main body portion and curving in a direction of curvature;
the second curve portion being positioned distally of the first curve portion;
the second curve portion curving in a direction of curvature that is opposite the direction of curvature of the first curve portion;
the second curve portion being more flexible than the first curve portion, the second curve portion possessing a vertex;
the third curve portion being positioned distally of the second curve portion, the third curve portion possessing a vertex;
the third curve portion curving in a direction opposite the direction of curvature of the second curve portion;
wherein a line contacting both the first curve portion and the third curve portion forms an obtuse angle with respect to the axis of the main body portion;
the line contacting both the first curve portion and the third curve portion is a first line, a second line parallel to the first line contacts the second curve portion;
the entirety of the guide wire between the vertex of the second curve portion and the vertex of the third curve portion is positioned between the first and second lines;
the first curved portion comprising a flat portion having a width and thickness, with the width of the flat portion being larger than the thickness of the flat portion, the first curved portion being more flexible than the main body portion; and the curved distal portion of the elongated member being configured to turn around, to advance in a main body of a blood vessel and to not erroneously enter a branch of the blood vessel when a most distal tip of the guide wire extends into the branch.

18. The guide wire according to claim 17, wherein the elongated member comprises a core wire and a resin coating portion covering the core wire and contacting the core wire, the core wire possessing a flat distal portion covered and contacted by the coating portion.

19. The guide wire according to claim 17, wherein the elongated member comprises a core wire and a resin coating portion covering the core wire and contacting the core wire, the core wire at the third curve portion is a flat portion.

20. The guide wire according to claim 19, wherein the third curve portion possesses a higher flexibility than the flexibility of the second curve portion.

* * * * *